United States Patent [19]
Gaba et al.

[11] Patent Number: 5,947,285
[45] Date of Patent: Sep. 7, 1999

[54] MEDICAL WASTE DISPOSAL CONTAINER

[75] Inventors: Rodolfo Gaba, Simi Valley; Michael Griffin, Aqua Dulce, both of Calif.; Ignaty Gusakov, East Aurora, N.Y.; Ruane S. Jeter, Los Angeles, Calif.; Brian Mach, Elma, N.Y.; Gordon H. Marsh, West Hills, Calif.

[73] Assignee: Graphic Controls Corporation, Buffalo, N.Y.

[21] Appl. No.: 08/969,075

[22] Filed: Nov. 12, 1997

Related U.S. Application Data

[60] Provisional application No. 60/031,016, Nov. 15, 1996, and provisional application No. 60/039,211, Feb. 28, 1997.

[51] Int. Cl.$^6$ .................................................. B65D 83/10
[52] U.S. Cl. ............................................. 206/366; 206/370
[58] Field of Search ................................... 206/365, 366, 206/370; 220/908, 910

[56] References Cited

U.S. PATENT DOCUMENTS

| | | |
|---|---|---|
| Re. 33,413 | 10/1990 | Hanifl . |
| 449,149 | 3/1891 | Whelan . |
| 457,918 | 8/1891 | Stevenson et al. . |
| 697,655 | 4/1902 | O'Leary . |
| 1,333,051 | 3/1920 | Young . |
| 4,032,037 | 6/1977 | Dubery et al. . |
| 4,315,592 | 2/1982 | Smith . |
| 4,453,648 | 6/1984 | Harris et al. . |
| 4,580,688 | 4/1986 | Harris et al. . |
| 4,714,168 | 12/1987 | Johnson et al. . |
| 4,715,498 | 12/1987 | Hanifl . |
| 4,779,728 | 10/1988 | Hanifl et al. . |
| 4,809,850 | 3/1989 | Laible et al. . |
| 4,828,107 | 5/1989 | Spencer . |
| 4,863,057 | 9/1989 | Hanifl et al. . |
| 4,890,733 | 1/1990 | Anderson . |
| 4,903,832 | 2/1990 | Stewart . |
| 4,927,076 | 5/1990 | Simpson . |
| 4,955,477 | 9/1990 | Bruno . |
| 5,076,429 | 12/1991 | Patrick et al. . |

(List continued on next page.)

FOREIGN PATENT DOCUMENTS

| | | |
|---|---|---|
| de. 85 03 511 | 6/1985 | Germany . |
| 473199 | 11/1937 | United Kingdom . |

OTHER PUBLICATIONS

"Sharps–A–Gator, Sharps Collection and Disposal System, Point–Of–Use Sharps Container," CA –4833–1, Devon Industries, Inc. (1992).

(List continued on next page.)

*Primary Examiner*—David T. Fidei
*Attorney, Agent, or Firm*—Ratner & Prestia

[57] ABSTRACT

A medical waste disposal system for contaminated products to be disposed having a hollow, disposal container and a housing enclosure which is engageable with and covers the container. The housing enclosure has an opening and a tumbler which is pivotally mounted to prevent access to the interior of the housing enclosure when a contaminated product is being deposited into the interior of the disposal container. In one embodiment, upon dropping waste into the opening of the housing enclosure, the tumbler rotates to simultaneously close the upper opening in the housing enclosure and open a lower opening which allows the waste to drop into the disposal container. After the waste has dropped, the tumbler, which is weighted, returns to its original position. When the disposal container reaches full capacity, the tumbler is blocked by the medical waste in the disposal container thereby preventing rotation to the open position. In an additional embodiment, a tumbler having an angled tip portion is provided which forms a lower passage to permit passage of waste while simultaneously blocking the accessibility beyond the interior of the housing enclosure without the need to fully rotate the tumbler to a closed position. The housing enclosure is also provided with a portion having a squared or sloping contour to prevent sharps from passing or being ejected back through the opening of the container. The housing enclosure also includes a lid having a lock securely closing the medical waste disposal system for final disposal.

50 Claims, 38 Drawing Sheets

U.S. PATENT DOCUMENTS

| | | |
|---|---|---|
| 5,080,251 | 1/1992 | Noack . |
| 5,178,322 | 1/1993 | Shillington . |
| 5,240,108 | 8/1993 | Tonna . |
| 5,387,735 | 2/1995 | Ponsi et al. . |
| 5,413,243 | 5/1995 | Bemis et al. . |
| 5,423,450 | 6/1995 | Shillington et al. . |
| 5,494,186 | 2/1996 | Marsh . |
| 5,603,404 | 2/1997 | Nazare et al. . |
| 5,605,245 | 2/1997 | Bemis et al. . |

OTHER PUBLICATIONS

"VHA x Plus Sharps Container," Sales Manual, VHA Supply Co. (1989).

"Sharps Container System Product Profile," Sherwood Medical (1989).

"STOP—Don't Get Stuck With an Obsolete Sharps Disposal System," Premium Plastics, Inc. (1988).

"Infection Control Illustrating Herculite of Devon Industries, Inc.," Hospital Purchasing News (1996).

"Bemis Delivers Exceptional Quality In The Sharps Disposal Units You Depend On," Bemis Maunfacturing Company (1996).

"Encore Sharps Collection Unit," Devon Industries, Inc. (Jul. 1996).

"In–Room Sharps Disposal System," Sage Products, Inc. (1993).

"VHA xPlus Sharps Disposal Containers," VHA Supply Co. (1991).

"How To Use The In–Room Wall Enclosure System," Sage Products, Inc. (1993).

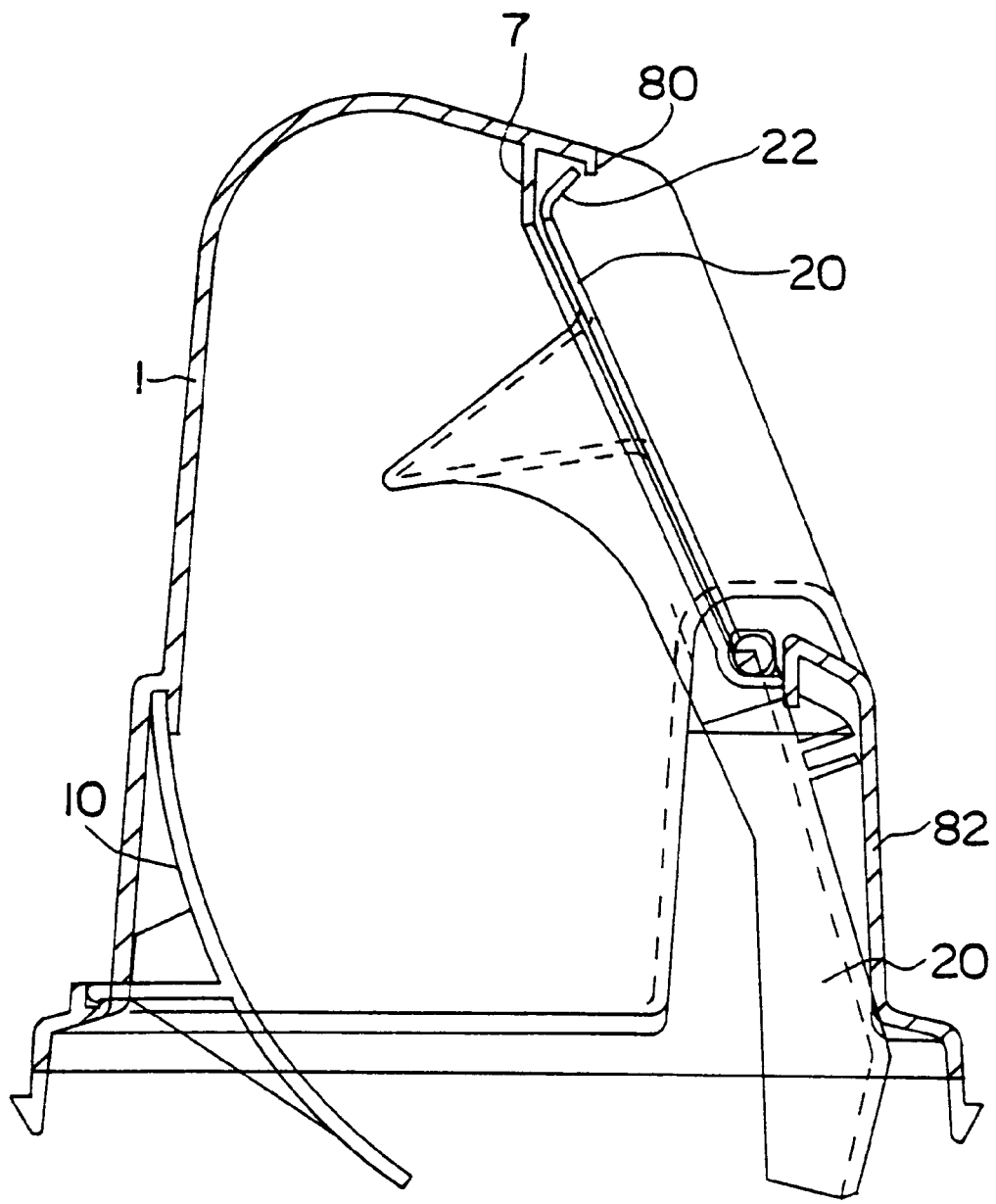
F I G. 21C

MEDICAL WASTE DISPOSAL CONTAINER

This application claims the benefit of U.S. Provisional application Ser. No. 60/031,016 filed Nov. 15, 1996 and U.S. Provisional application Ser. No. 60/039,211 filed Feb. 28, 1997.

FIELD OF THE INVENTION

The present invention relates generally to the disposal of contaminated items and, in particular, to a disposal system for use in a hospital or similar environment where contaminated items must be collected and disposed without creating a hazard for patients or hospital personnel.

BACKGROUND OF THE INVENTION

In hospitals, clinics, and similar medical institutions, contamination continues to be of utmost concern. The prevention of the spread of communicable diseases is a major priority; therefore, disposable, single-use, patient care products have become prevalent. Such items are contaminated, once used, and can readily transmit disease. The items include such devices as hypodermic needles, intravenous needles, razors, scalpel blades, or other sharps—all of which are required to be disposed at their point of usage under current guidelines of the United States Centers for Disease Control.

Various disposal containers for medical wastes have been disclosed for the purpose of preventing an individual from access to contaminated items such as sharps once the wastes have been deposited into the container. One example of a prior art sharps container is disclosed in U.S. Pat. No. Re. 33,413 issued to Hanifl having a hollow, outer enclosure with an elongated slot inlet at the top. A barrier adjacent the slot restricts access to the interior of the enclosure. An inner container having an inlet is inserted into the outer enclosure such that the inlet is aligned with the slot upon insertion. The inner container includes a pivotal closure which may be locked in place when full in order to prevent access to the contents of the container. As disclosed in the patent, the barrier on the outer enclosure is a shelf and a cowl combination which together define an opening. The barrier makes it difficult for an adult human hand to pass through the opening. This system is not entirely effective, however, in preventing access to sharps within the container.

Another example of a sharps disposal container is provided by U.S. Pat. No. 5,387,735, issued to Ponsi et al. This patent also includes a barrier and pivotal closure disposed near an opening of a container body. The pivotal closure is shaped to include a retention pocket which prevents sharps from being dispensed through the opening from the interior of the container when the container is upright. The retention pocket is required to reduce the possibility of injury by helping to prevent ejection of sharps out of the container. Also described are locking tabs which are integral with the pivotal closure and provide for locking the closure in a closed position before disposal of a container which is filled. The disposal system of Ponsi et al., however, like the sharps container of Hanifl, also suffers from a somewhat limited protection against access to sharps within the container. Consequently, improper reuse and possible contamination can ensue. The medical waste disposal container according to the present invention overcomes the limitations, difficulties, and shortcomings of these prior art devices by providing a safe way for health care workers to dispose of used or contaminated sharps, such as hypodermic needles, intravenous needles, razors, and scalpel blades, as well as other contaminated products.

SUMMARY OF THE INVENTION

The present invention provides a secure, readily accessible system for the disposal of contaminated products. The system includes a hollow, disposal container and a housing enclosure which is engageable with and covers the container. An upper opening is provided at the top of the housing enclosure for permitting access to its interior. The housing enclosure is provided with a tumbler which prevents access to the interior of the housing enclosure when a contaminated product is being deposited into the interior of the disposal container. In one embodiment, upon dropping waste into the opening of the housing enclosure, the tumbler is rotated to simultaneously close off the upper opening in the housing enclosure and open a lower opening to the disposal container to permit the waste to drop into the disposal container. After the waste has dropped, the tumbler, which is weighted, returns to its original position. When the disposal container reaches full capacity, the tumbler is configured so that it is blocked by the medical waste in the disposal container and will not return to the open position but remains rotated in a closed position.

In an additional embodiment, a tumbler having an angled tip portion is provided which forms a lower passage to permit waste to pass while simultaneously blocking accessibility beyond the interior of the housing enclosure without the need to fully rotate the tumbler to a closed position.

Another feature of the disposal container according to the present invention is that the back of the housing enclosure has a portion with a squared or sloping contour which helps to prevent sharps from returning through or being ejected from the opening of the container. In order to further impede or prevent access to the interior of the disposal container after it has been filled, the housing enclosure of the present invention also includes a lid having a lock for securely closing the medical waste disposal system for final disposal.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 10I is a view similar to FIG. 10H, but with the tumbler further rotated to continue blocking the upper opening in the housing enclosure from access;

FIG. 21C is an enlarged partial cross-sectional side view of the housing enclosure and tumbler of the medical waste disposal system shown in FIGS. 21A and 21B in the locked position.

DETAILED DESCRIPTION OF THE INVENTION

Figure 1:
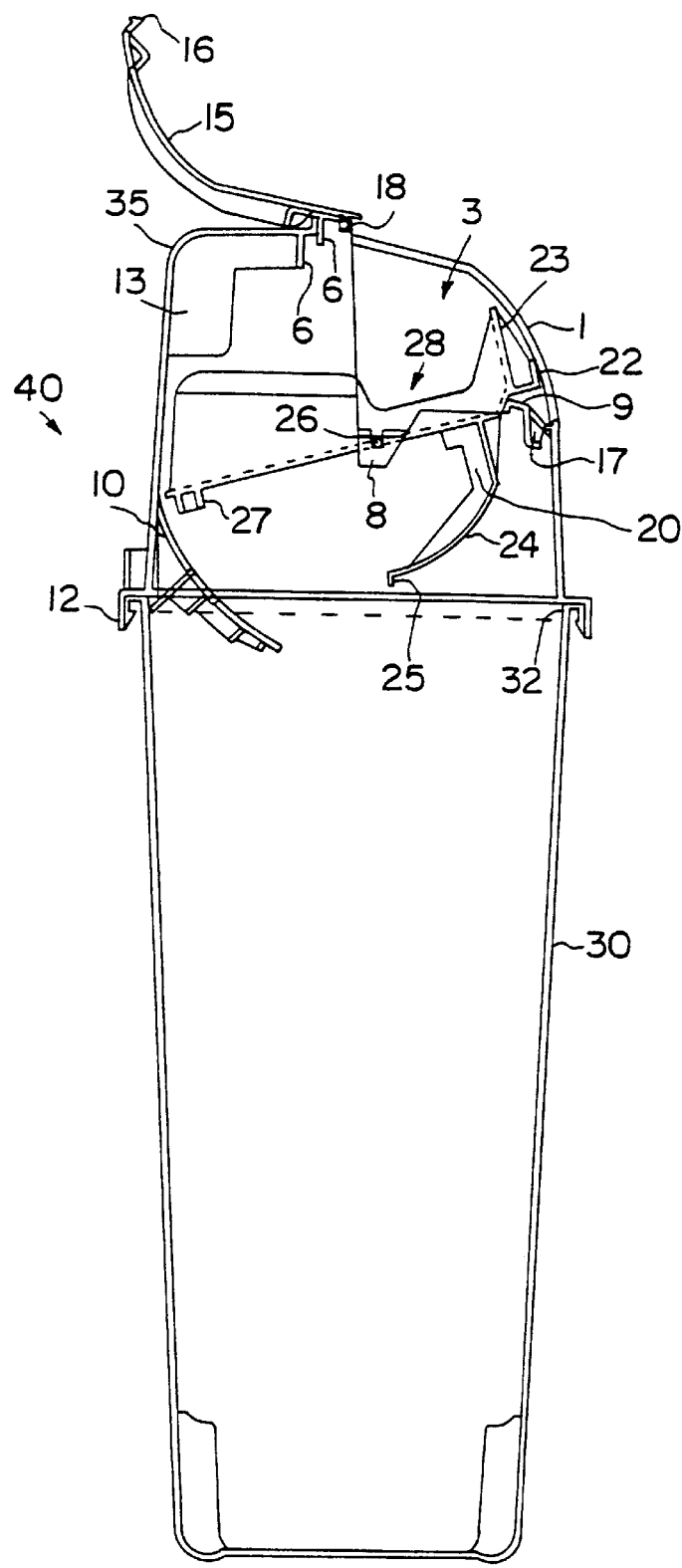
FIG. 1 is a cross-sectional side view of a medical waste disposal system according to the invention, with one form of tumbler located within a hollow housing enclosure having a lid, and with the tumbler in the housing enclosure in a fully open position.

Referring now to the drawing, wherein like reference numerals refer to like elements throughout, FIG. 1 shows a medical waste disposal system 40 according to the present invention having a hollow housing enclosure 1 and a hollow disposal container 30 which are attached to each other and having a tumbler or pivotal closure 20 pivotally mounted within housing enclosure 1. Housing enclosure 1 is provided with a flap or ramp 10 which extends beneath housing enclosure 1 and into disposal container 30 as shown. Also shown in FIG. 1 are ribs 13 which reinforce the upper back interior portion of housing enclosure 1 and extend parallel to the cross-sectional plane of FIG. 1.

Tumbler 20 of the present invention forms a barrier which restricts access by a user both to the interior of housing enclosure 1 and to the interior of disposal container 30 when tumbler 20 is rotated to dispose of a sharp 42 (see FIG. 4A) deposited in housing enclosure 1. Tumbler 20 is pivotally mounted inside housing enclosure 1 by pivot pins 26 engaged in pivot brackets 8 formed on the interior of housing enclosure 1. By this construction, tumbler 20 can pivot about a pivot axis extending through opposite pivot pins 26. Although disclosed with respect to the use of pivot pins 26 and pivot brackets 8, it will be readily recognized by those of ordinary skill that other pivoting mechanisms may also be incorporated. As used in this application, the name "tumbler" refers to a pivoting mechanism which (a) closes and opens access to both the interior of housing enclosure 1 and the interior of disposal container 30, and (b) transfers sharp 42 from one position to another. At least one source of the name is the tumbling action which sharp 42 undergoes as it is transferred from outside housing enclosure 1 to the interior of disposal container 30 along tumbler 20; specifically, sharp 42 may somersault as it falls downward.

Figure 9A:
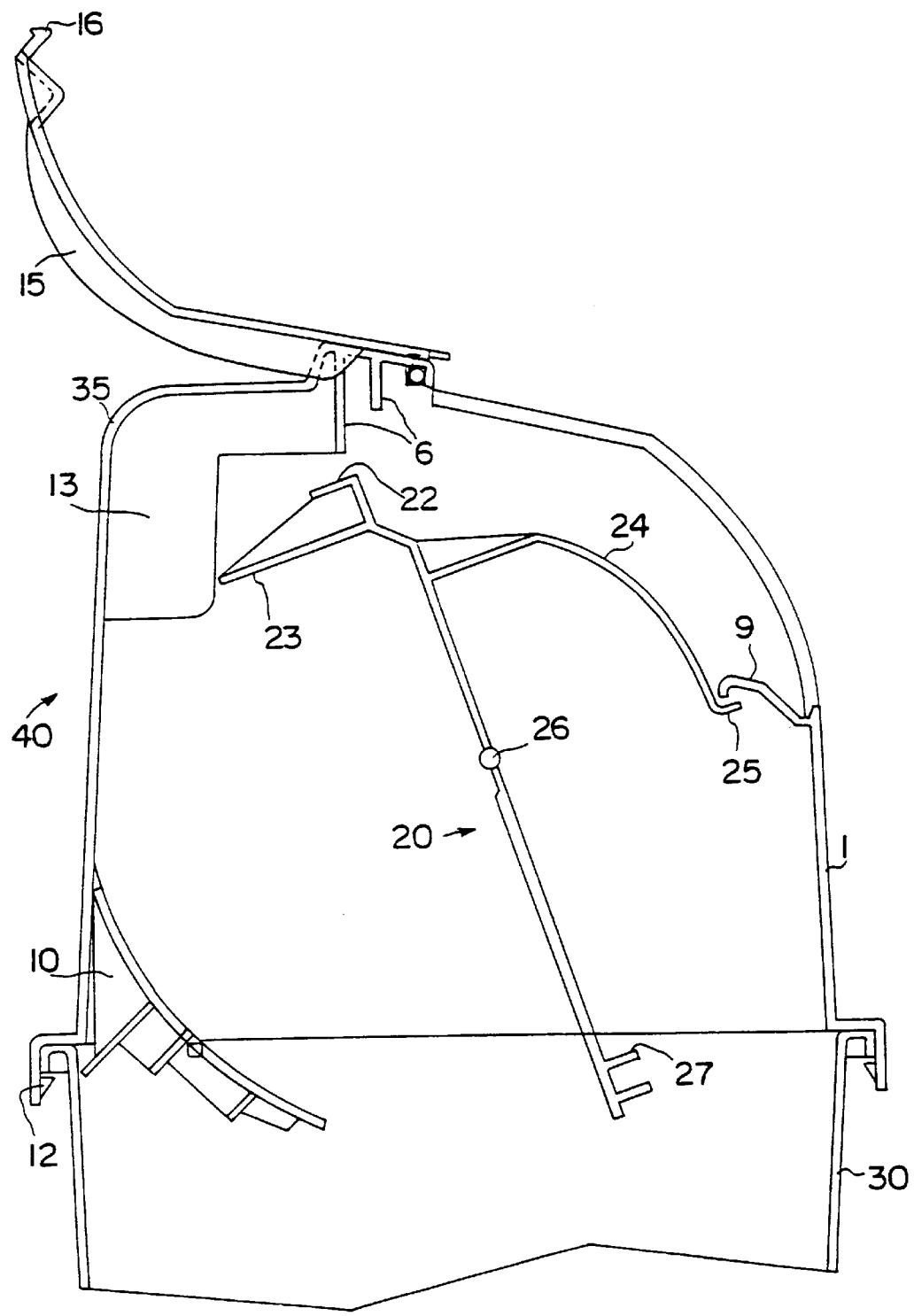
FIG. 9A is an enlarged cross-sectional side view of the medical waste disposal system shown in FIG. 1, showing the tumbler in the housing enclosure constrained from overrotation.
Figure 9B:
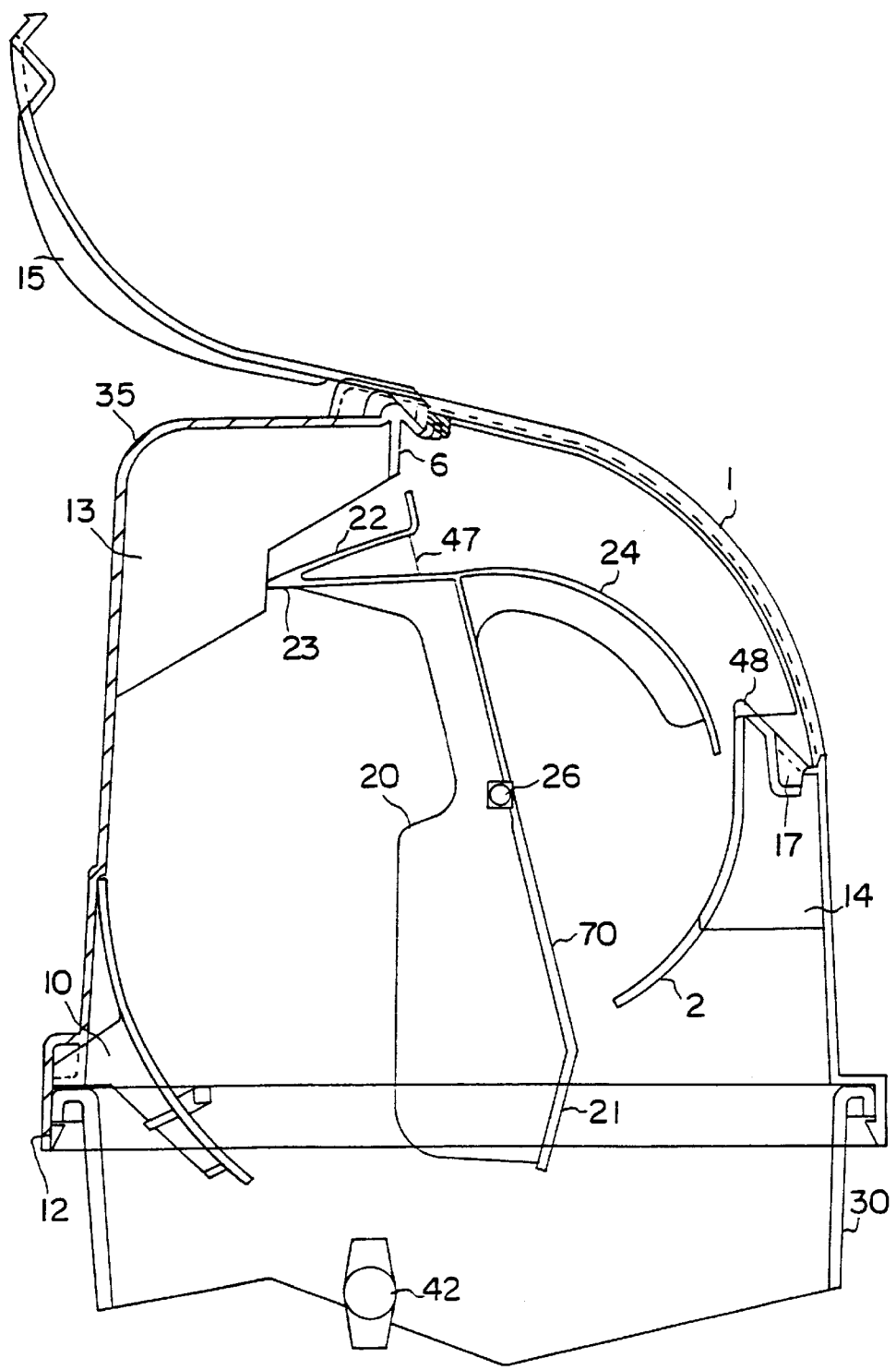
FIG. 9B is an enlarged cross-sectional side view of an alternative medical waste disposal system according to the invention, having a tumbler with an angled tip portion, a housing enclosure having a scoop and an alternative rib configuration, and with the tumbler in the housing in the fully rotated position.

FIGS. 2A, 2B, 2C, 2D, 2E, and 2F respectively show a partial cross-sectional side view, a sectional planar view, a front planar view, a side view, a top planar view, and a bottom planar view of housing enclosure 1 of medical waste disposal system 40 shown in FIG. 1 with flap 10 removed for clarity in FIGS. 2B–2F. Ribs 13 are substantially flat projections of finite thickness which, as discussed above, extend parallel with the cross-sectional plane of FIG. 1, and are shown in detail in FIGS. 2A–2F. Typically three ribs 13 are used. In addition to reinforcing housing enclosure 1, ribs 13 may also be used to prevent over-rotation of tumbler 20 as shown in FIGS. 9A and 9B and discussed in detail below. Also shown in FIGS. 2A–2F are reinforcing projections 6 which are provided to increase the rigidity of housing enclosure 1. Additional reinforcement may also be provided in other areas of housing enclosure 1 by adding ribs 14 which are substantially flat projections of finite thickness as shown in FIGS. 2C, 2D, 2E, and 2F.

Figure 2A:
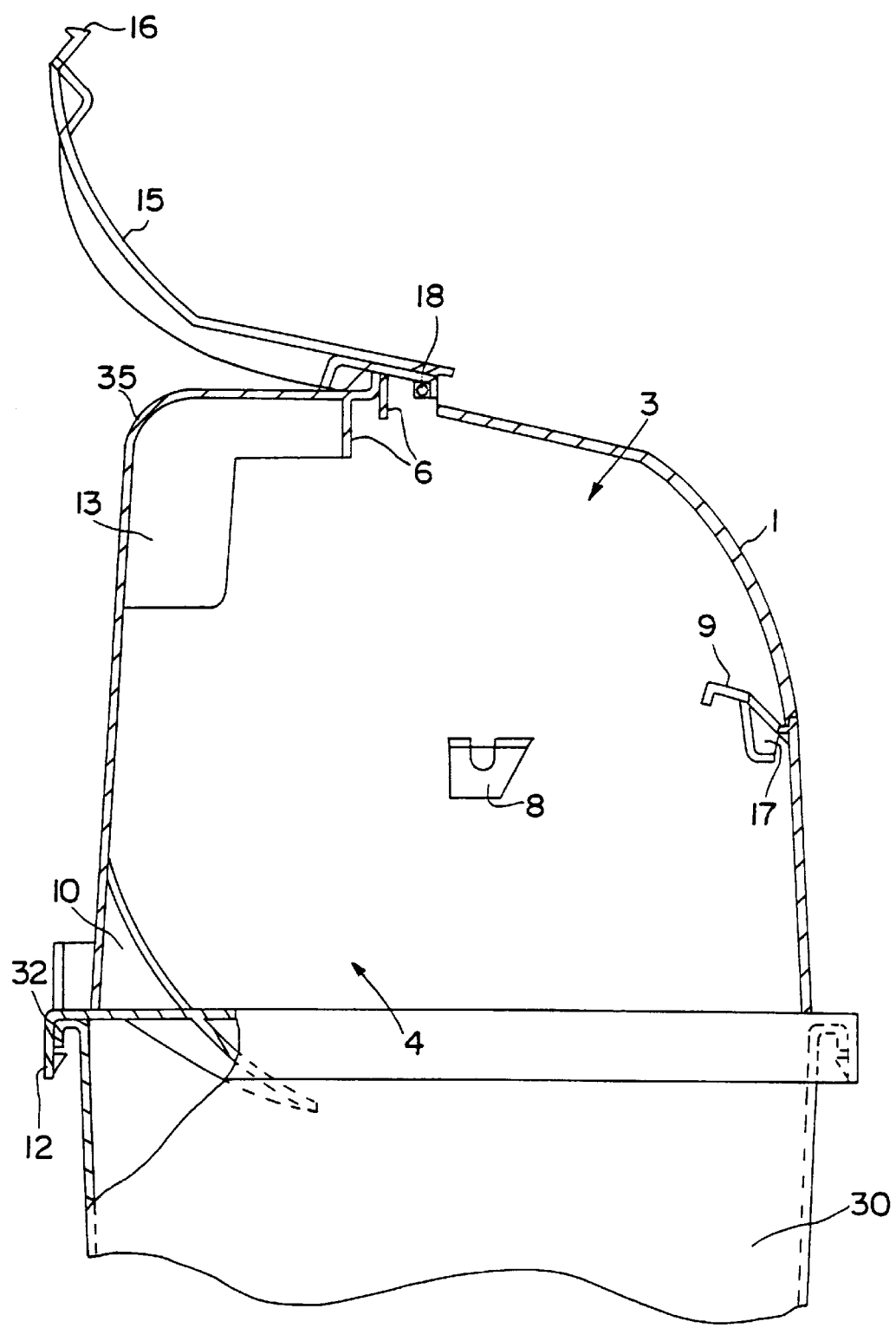
FIG. 2A is an enlarged partial cross-sectional side view of the housing enclosure, lid, and disposal container of the medical waste disposal system shown in FIG. 1.
Figure 2B:
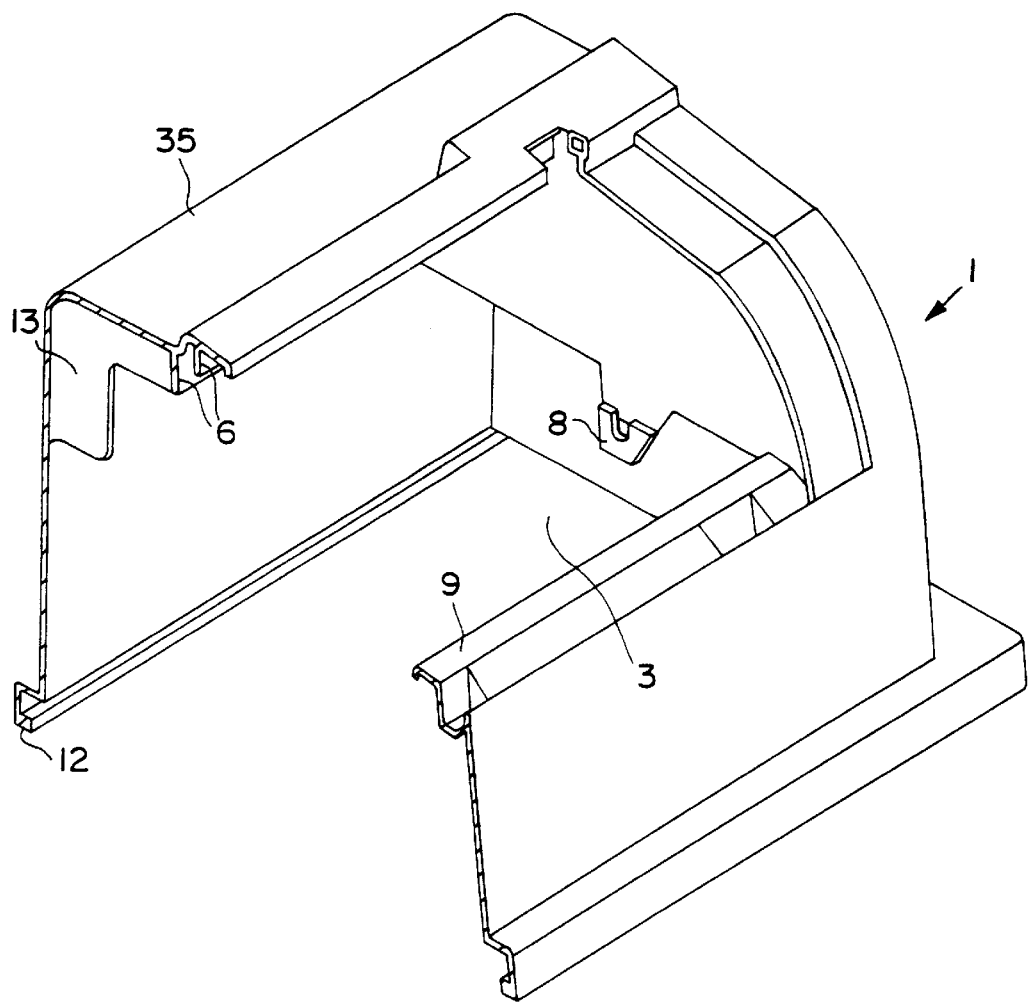
FIG. 2B is a sectional planar view of the housing enclosure shown in FIG. 2A.
Figure 2C:
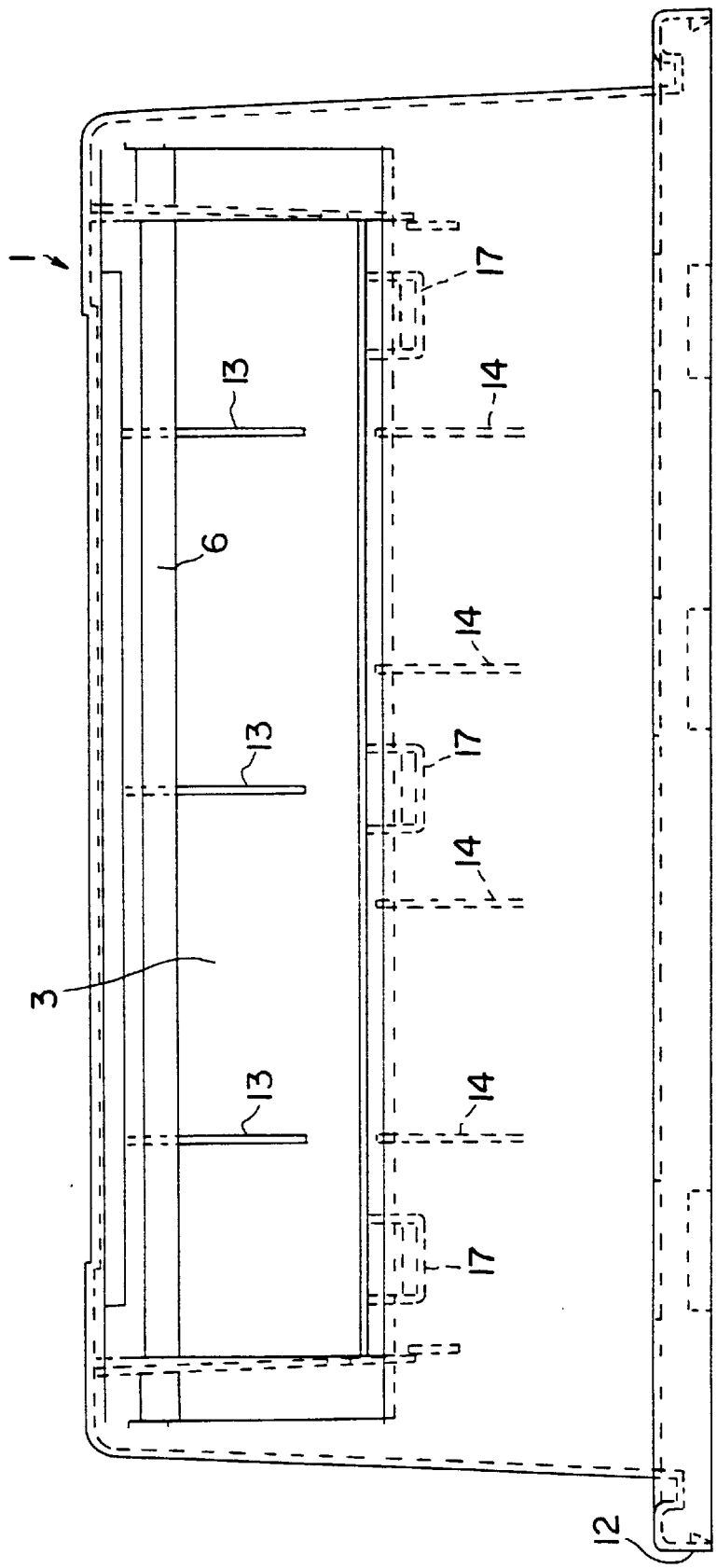
FIG. 2C is a front planar view of the housing enclosure shown in FIG. 2A.
Figure 2D:
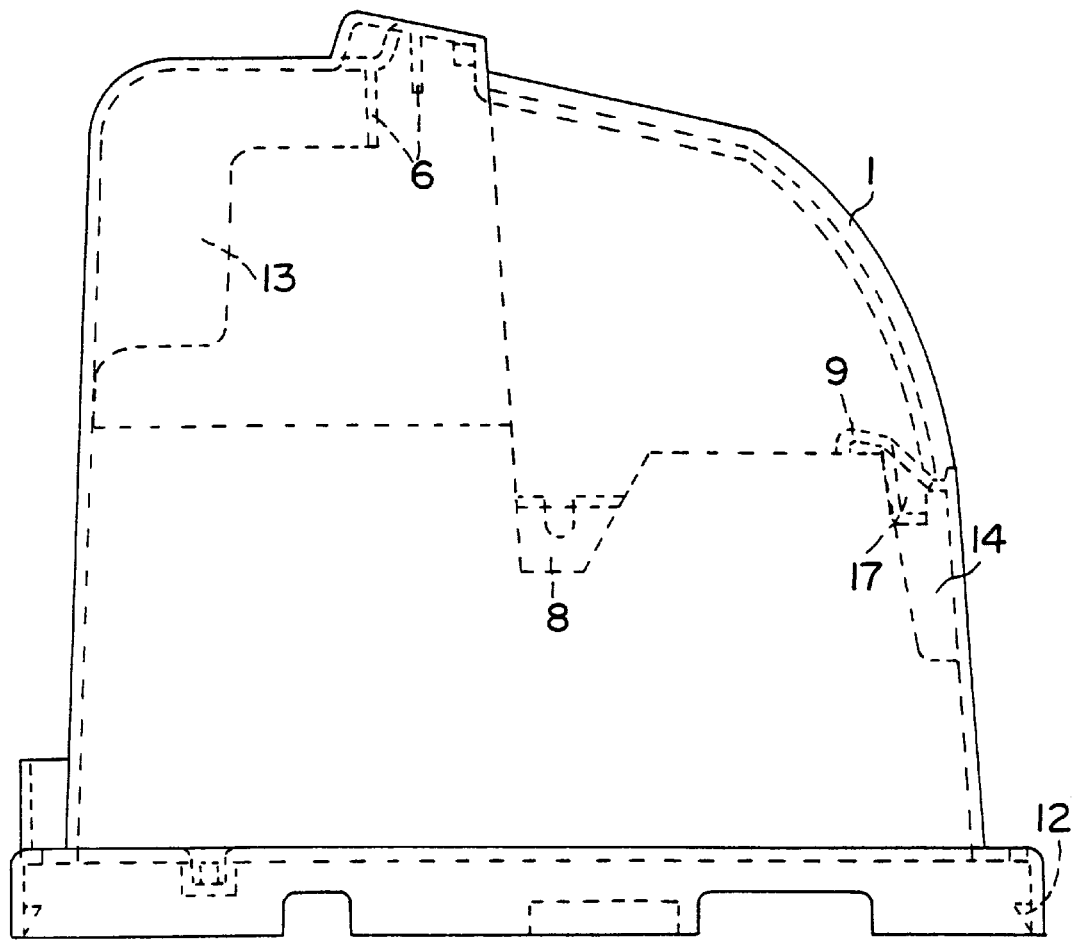
FIG. 2D is a side view of the housing enclosure shown in FIG. 2A.
Figure 2E:
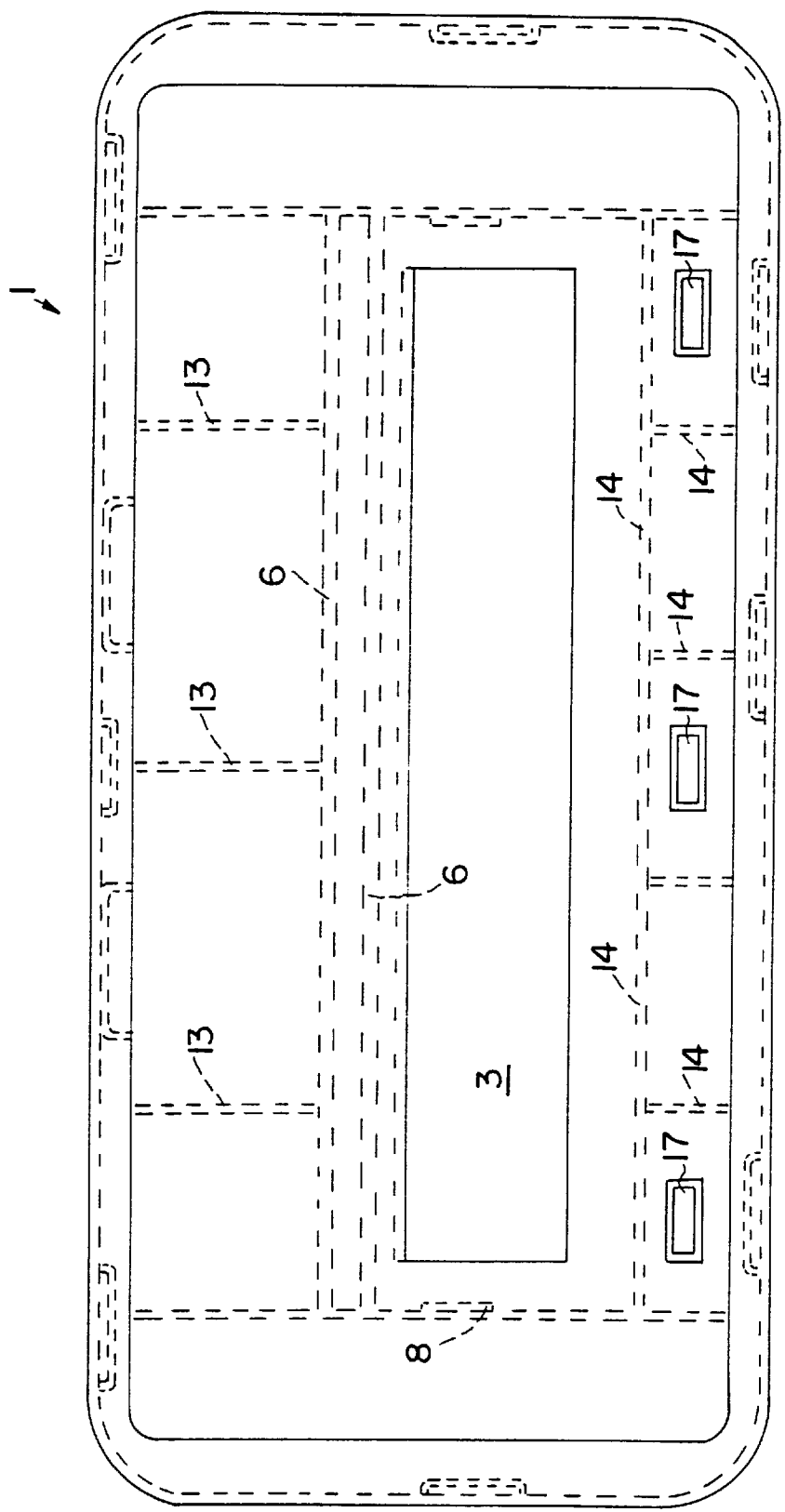
FIG. 2E is a top planar view of the housing enclosure shown in FIG. 2A.
Figure 2F:
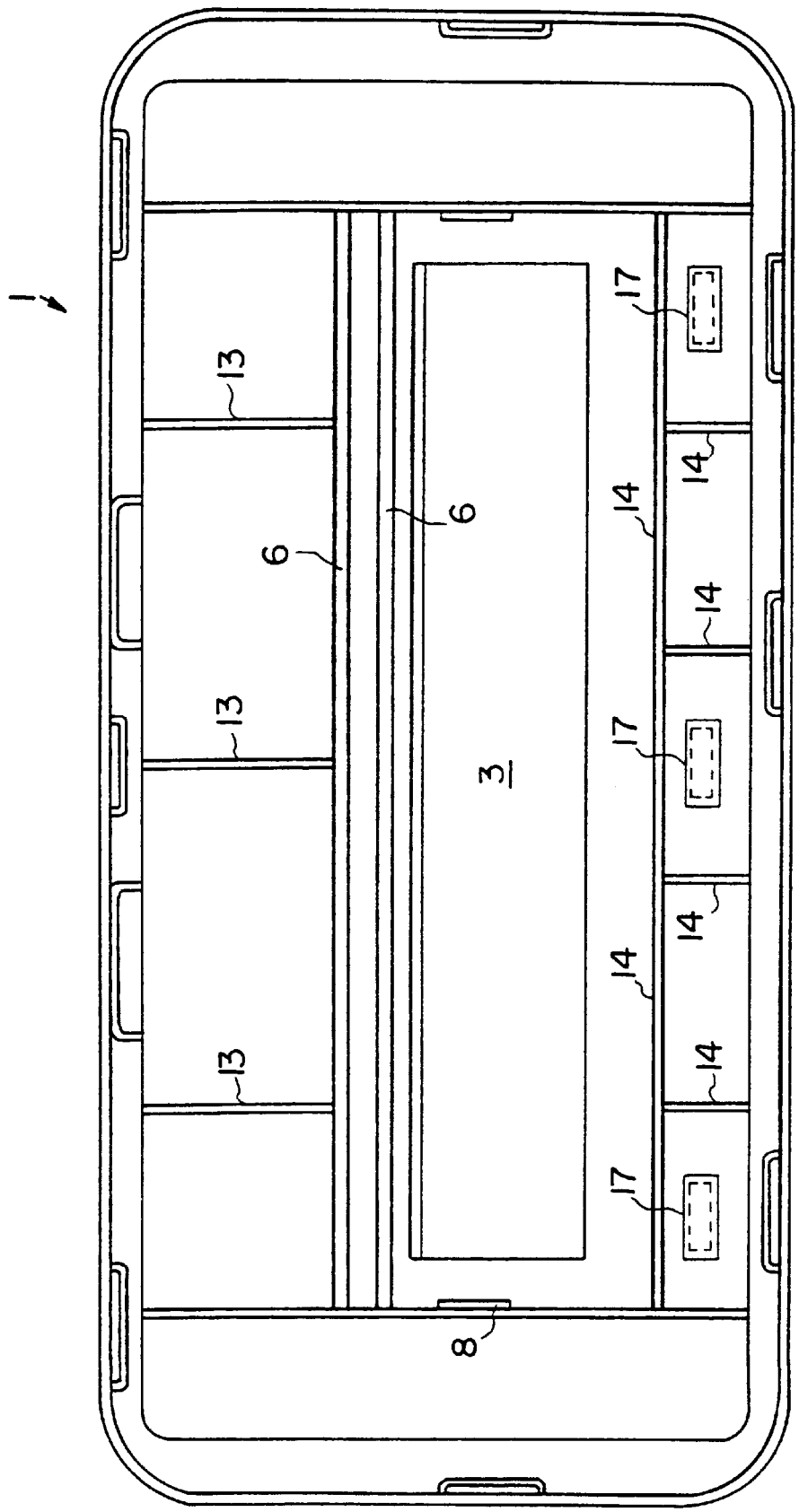
FIG. 2F is a bottom planar view of the housing enclosure shown in FIG. 2A.

As shown in FIG. 2A, disposal container 30 is preferably snap-fitted onto housing enclosure 1 in a conventional fashion as shown by lip 32 of disposal container 30 which is engaged by snap-tab 12 of housing enclosure 1. Other attachment mechanisms can be used as desired. Upper opening 3 is provided in housing enclosure 1 to permit access to the interior of housing enclosure 1 for depositing sharps or other medical waste products to be disposed. Lower opening 4 is provided by the hollow of housing enclosure 1 to permit the sharps or medical waste products deposited to pass to disposal container 30. Pivot brackets 8 and flap 10 are attached to the interior of housing enclosure 1 which, depending on manufacturing capabilities and the desire of the user, may be formed integrally (i.e., in one piece) or may be separately constructed and then attached to housing enclosure 1.

Figure 3:
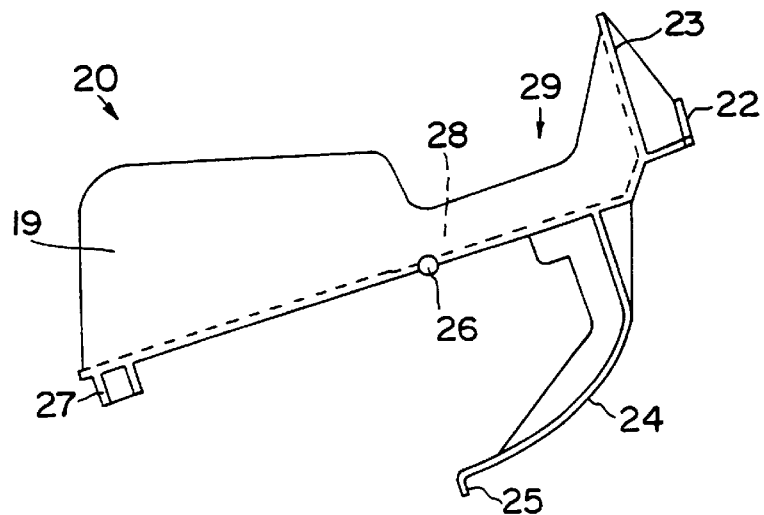
FIG. 3 is an enlarged cross-sectional side view of the tumbler of the medical waste disposal system shown in FIG. 1.

FIG. 3 shows in greater detail a cross-sectional side view of tumbler 20 of medical waste disposal system 40 shown in FIG. 1. Tumbler 20 includes an upper portion 23 and a curved lower portion 24 which are dimensioned so that together they extend across upper opening 3 of housing enclosure 1 when mounted and rotated in housing enclosure 1. Upper portion 23 and curved lower portion 24 may be used to prevent over-rotation of tumbler 20 as discussed in detail below. Curved lower portion 24 has curvature sufficient to rotate within the curvature of housing enclosure 1 and also includes a flange 25 for engaging lower stop 9 of housing enclosure 1 shown in FIG. 2A.

To facilitate rotational movement of tumbler 20, upper portion 23 also includes a grip 22 to allow the user to readily manipulate tumbler 20 when using disposal system 40. Grip 22 may be provided in a variety of configurations and is not necessarily confined within the interior of housing enclosure 1. As shown, for example, in FIG. 11, grip 22 may extend outside of and may be configured to engage a portion of the wall of housing enclosure 1. To provide for unimpeded rotation of tumbler 20, a chute 28 is defined between a pair of opposed side walls 19 in tumbler 20 to ensure that any sharps to be disposed do not become wedged during rotation of tumbler 20.

Medical waste disposal system 40 according to the present invention operates to allow waste to be loaded into upper opening 3 of housing enclosure 1, where it causes tumbler 20 to rotate. In a first embodiment, as tumbler 20 rotates, it simultaneously closes off upper opening 3 and opens lower opening 4 in housing enclosure 1 to allow the waste to drop into disposal container 30. After the waste has dropped, tumbler 20 is weighted to return to its original position. Thus, by permitting only upper opening 3 or lower opening 4 to be substantially opened at any given point in time, tumbler 20 prevents the hand of a user from following the same path into disposal container 30. Tumbler 20 can lock to prevent access to the interior of housing enclosure 1 and disposal container 30 once disposal container 30 is filled. To further secure disposal system 40, lid 15 can be closed as described in greater detail below.

Figure 4A:
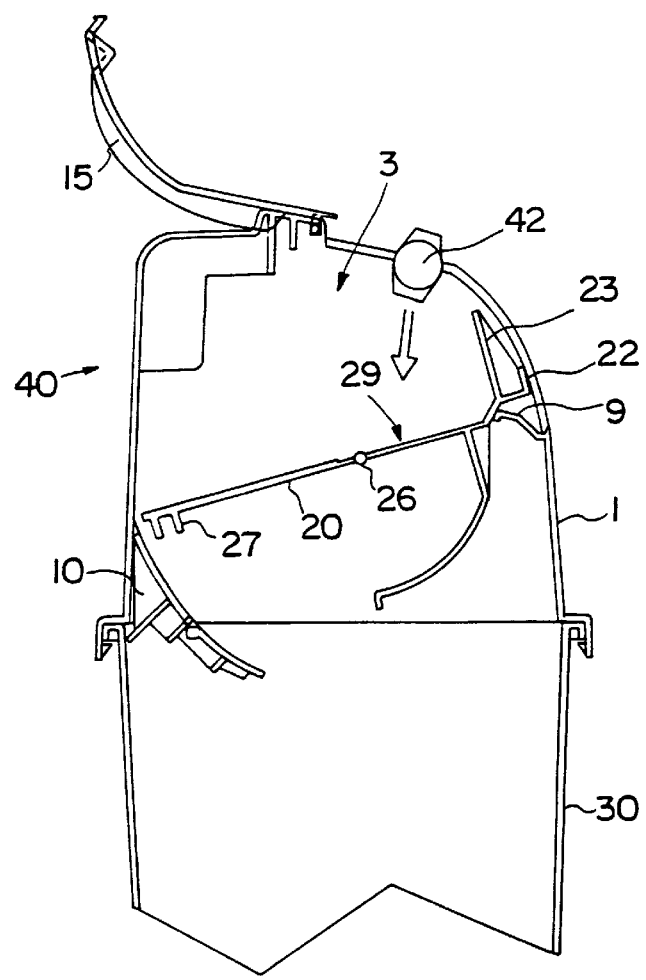
FIG. 4A is an enlarged cross-sectional side view of the medical waste disposal system shown in FIG. 1, with the tumbler in the housing enclosure in a fully open position and being loaded with a sharp to be disposed.
Figure 4B:
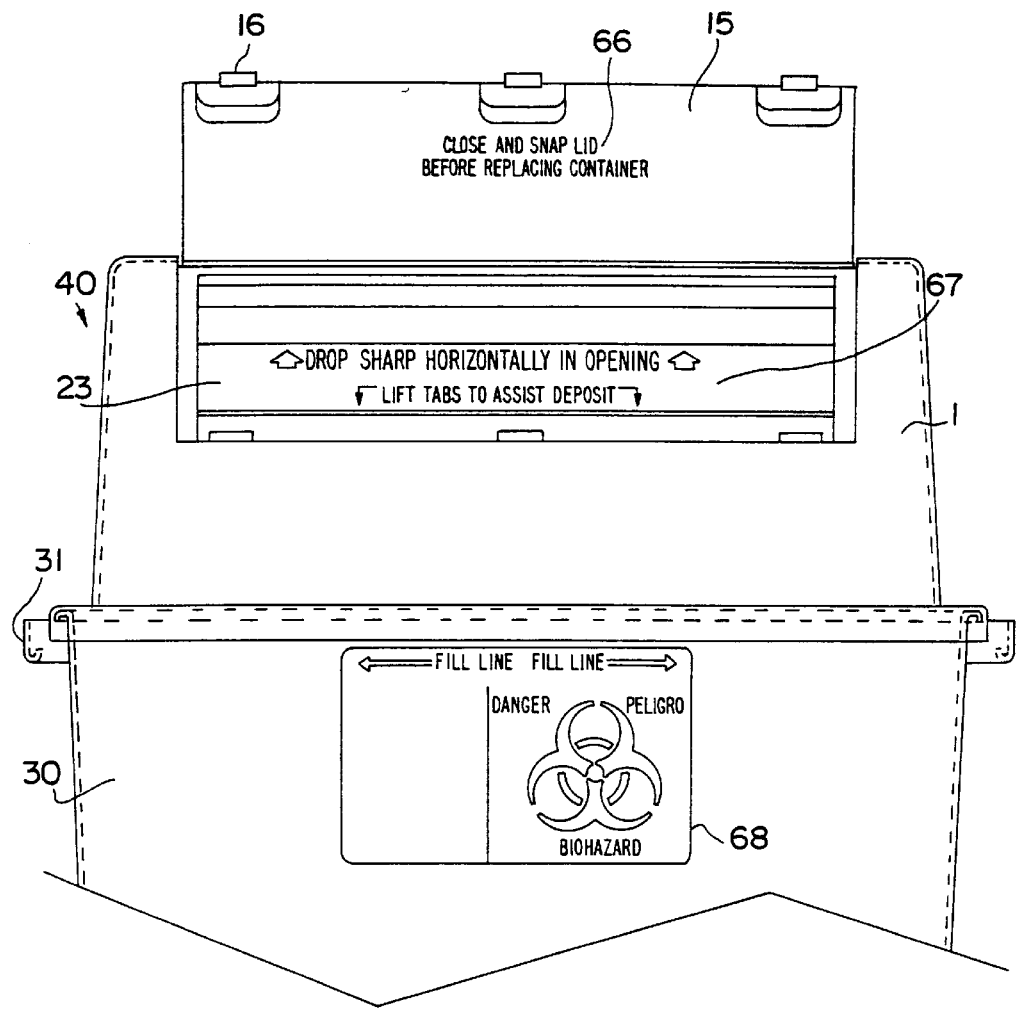
FIG. 4B is a front planar view of the medical waste disposal system shown in FIG. 4A.

Use of the medical waste disposal system 40 in the various stages of the disposal process according to a first embodiment of the present invention will become readily apparent upon inspection of FIGS. 4A, 4B, 5–7, 8A–8D, and 9A, and as now described. As shown in FIGS. 4A and 4B, when lid 15 and tumbler 20 are in the open position, a used sharp 42 may be passed through upper opening 3 of housing enclosure 1 and placed on an outer portion 29 of tumbler 20, typically one at a time. Counterweight 27 is provided on tumbler 20 for adjusting the center of gravity of tumbler 20 to bias it in the inclined and open orientation shown in FIG. 4A prior to loading.

FIG. 4B illustrates the use of various instructions, directions, and signs to provide information to the user. Specifically, lid 15 may have instructions 66 on its inner surface advising the user, for example, to "CLOSE AND SNAP LID BEFORE REPLACING CONTAINER." Upper portion 23 of tumbler 20 may have directions 67 advising the user, for example, to "DROP SHARP HORIZONTALLY IN OPENING," "LIFT TABS TO ASSIST DEPOSIT," or both. Directions 67 may include arrows pointing the user in an appropriate direction. Finally, disposal container 30 may have a sign 68 on its outer surface illustrating a recommended fill line and providing the user with cautionary information.

Figure 5:
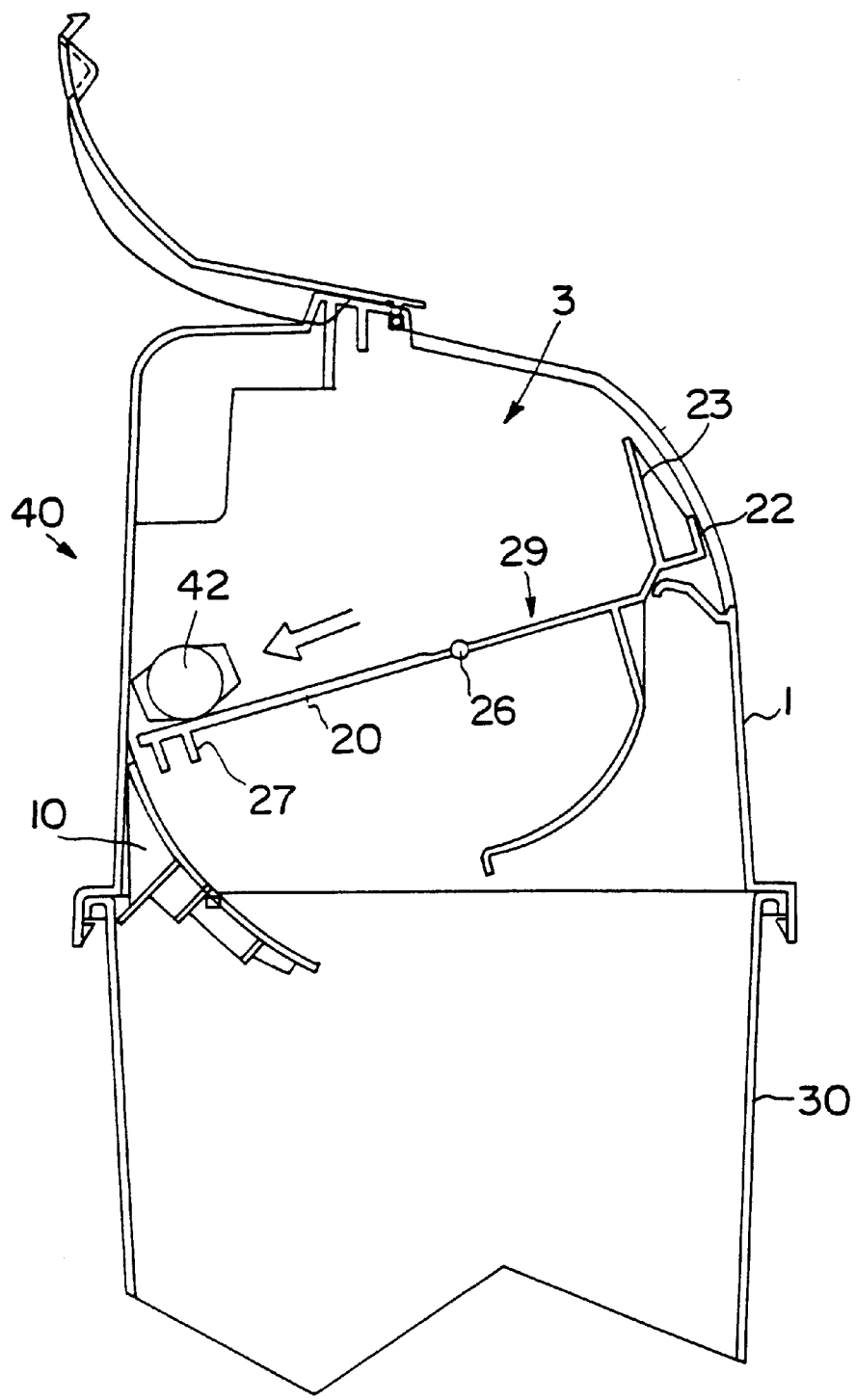
FIG. 5 is a view similar to FIG. 4, but with the sharp to be disposed traveling along the tumbler in the housing enclosure.
Figure 6:
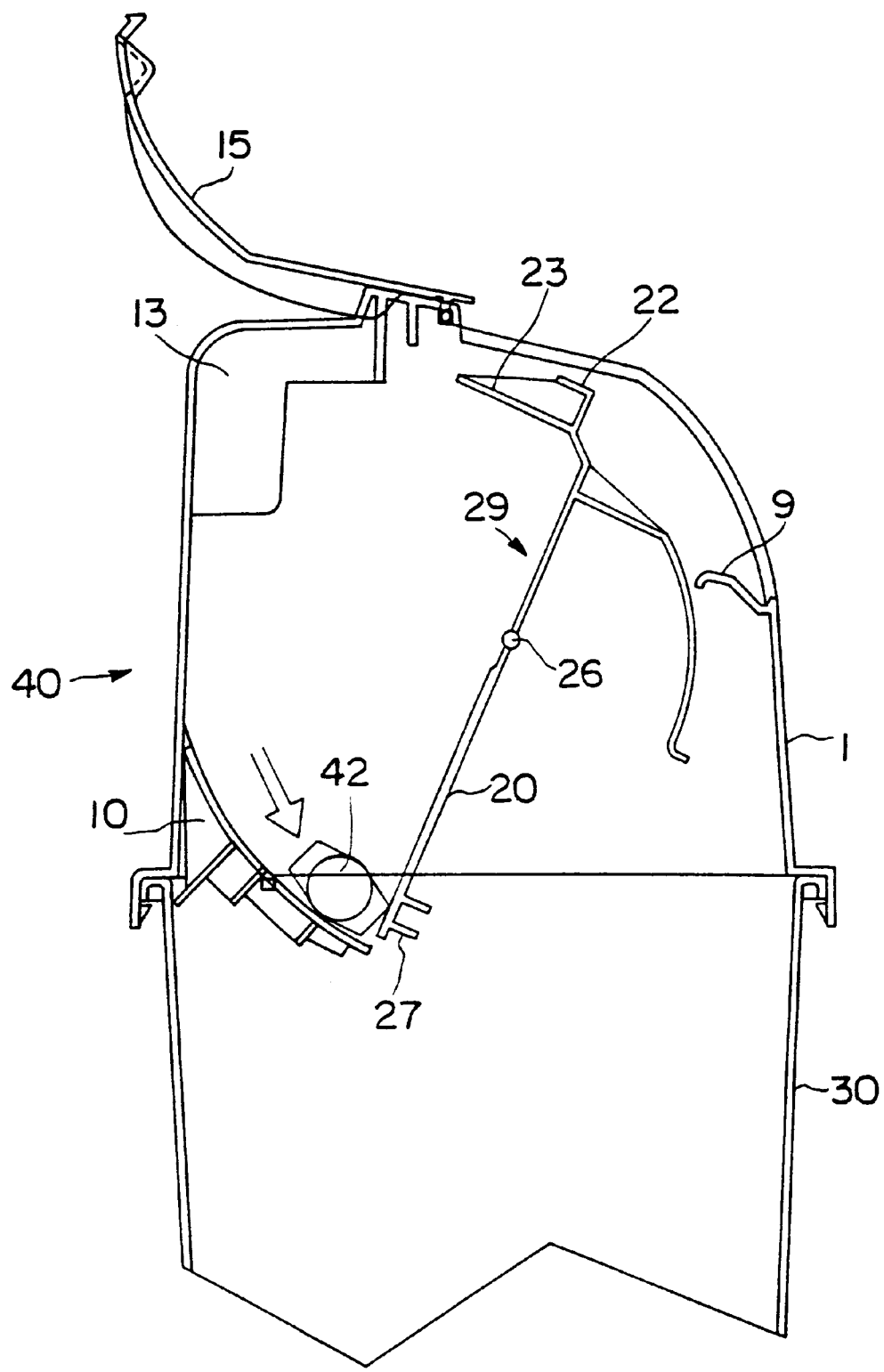
FIG. 6 is a view similar to FIG. 5, but with the tumbler in the housing enclosure approaching the closed position by rotation caused by the weight of the sharp being disposed.
Figure 7:
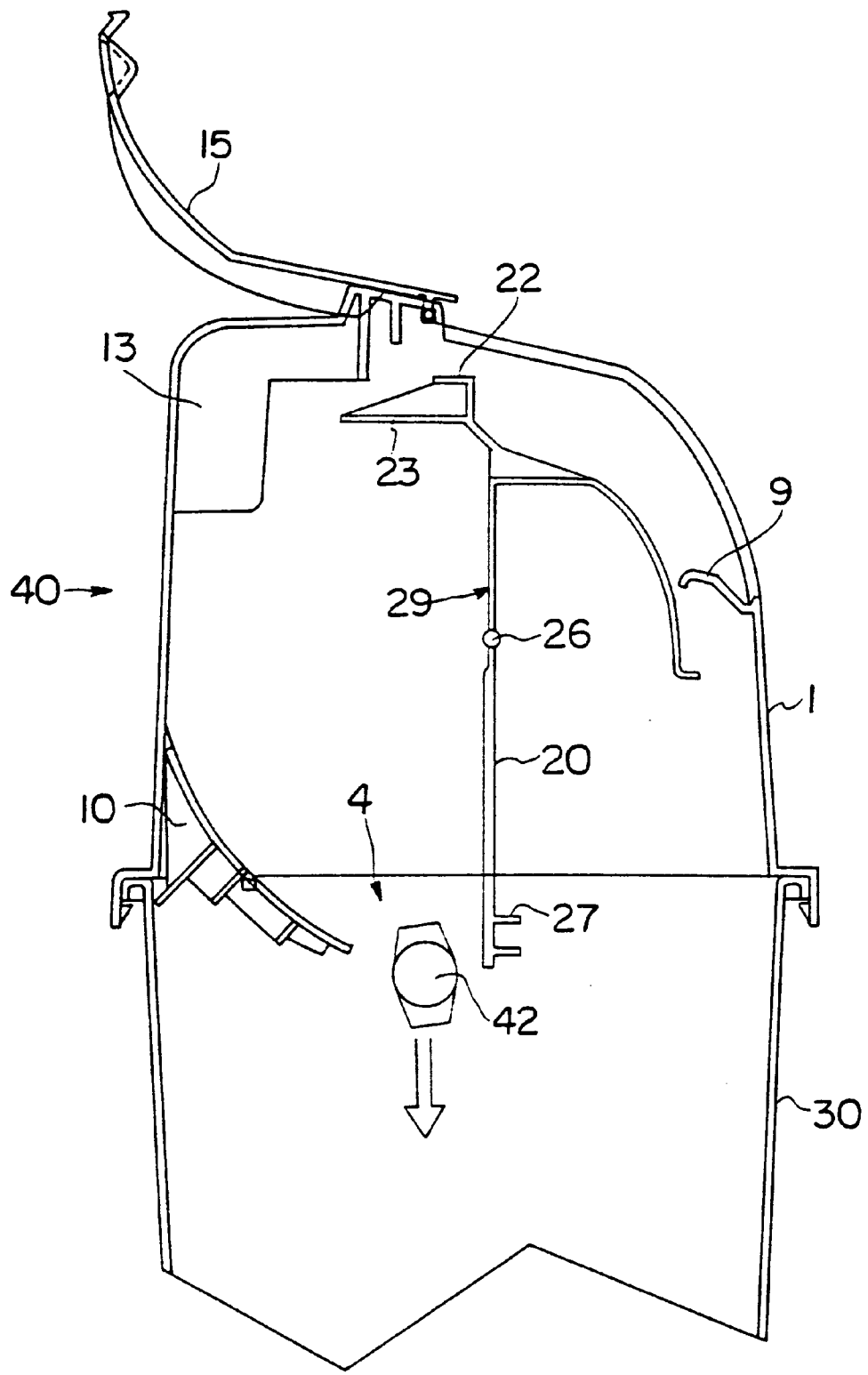
FIG. 7 is a view similar to FIG. 6, but with the tumbler closing an upper opening in the housing enclosure and permitting the sharp to pass through a lower opening into the disposal container before returning to the open position.

As shown in FIG. 5, any sharps 42 which are deposited slide away from upper portion 23 of tumbler 20 toward the back of housing enclosure 1. If sufficiently massive, the weight of any sharps 42 which are deposited causes tumbler 20 to pivot as shown in the sequence of FIGS. 6 and 7, thereby dropping sharps 42 within disposal container 30. Counterweight 27 may be adjusted so that rotation occurs upon the placement of a predetermined weight of sharps on tumbler 20. If sharp 42 does not have sufficient weight to overbalance the counterbalancing of counterweight 27, the user can manually cause sharp 42 to fall within disposal container 30 in exactly the same fashion. This is accomplished by grasping and moving grip 22 to pivot tumbler 20 upwardly in relation to grip 22, to cause sharp 42 to fall into disposal container 30.

Figure 8A:
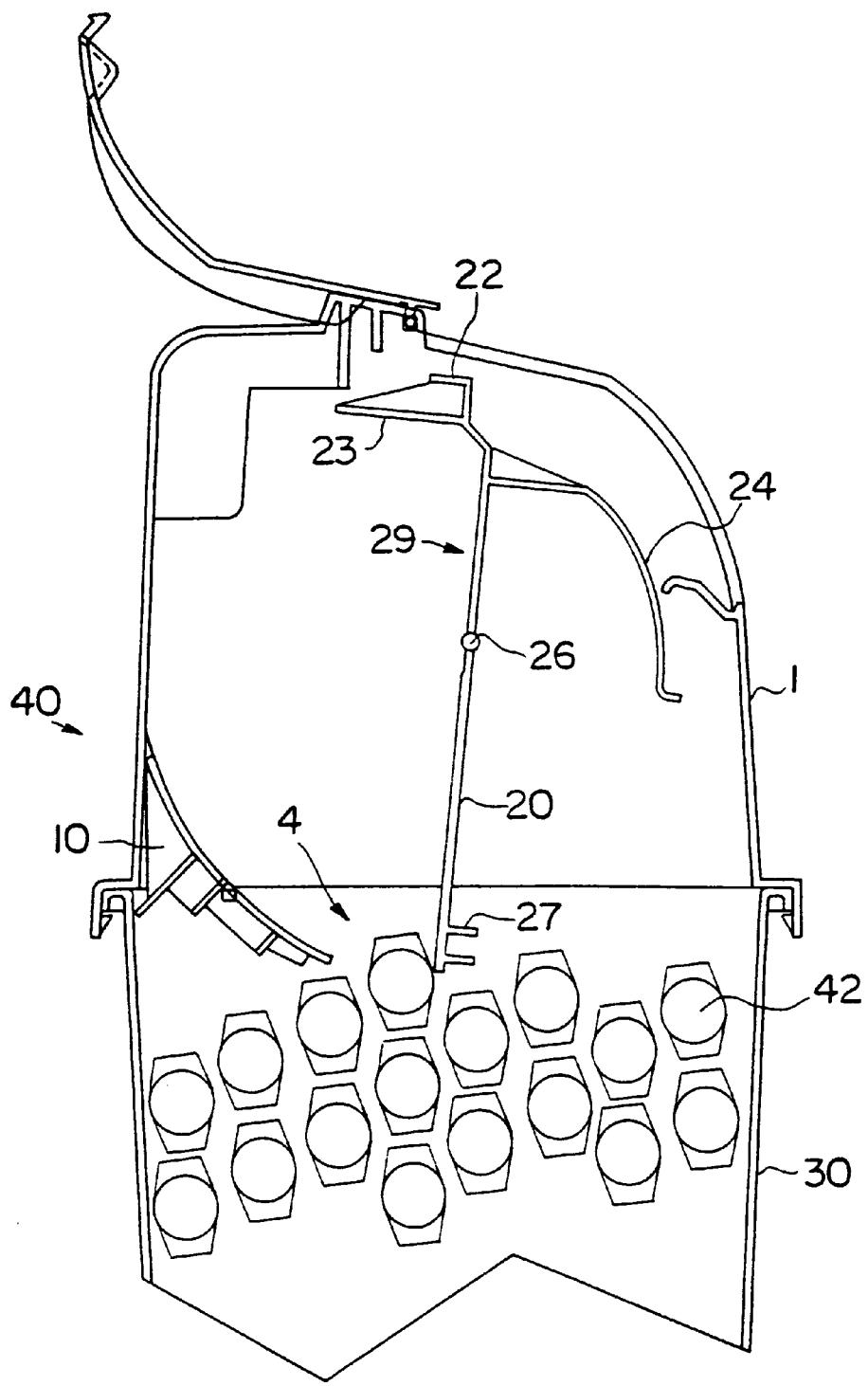
FIG. 8A is a view similar to FIG. 7, but with the tumbler blocked from returning to an open position in the housing enclosure by the sharps which fill the disposal container.
Figure 8B:
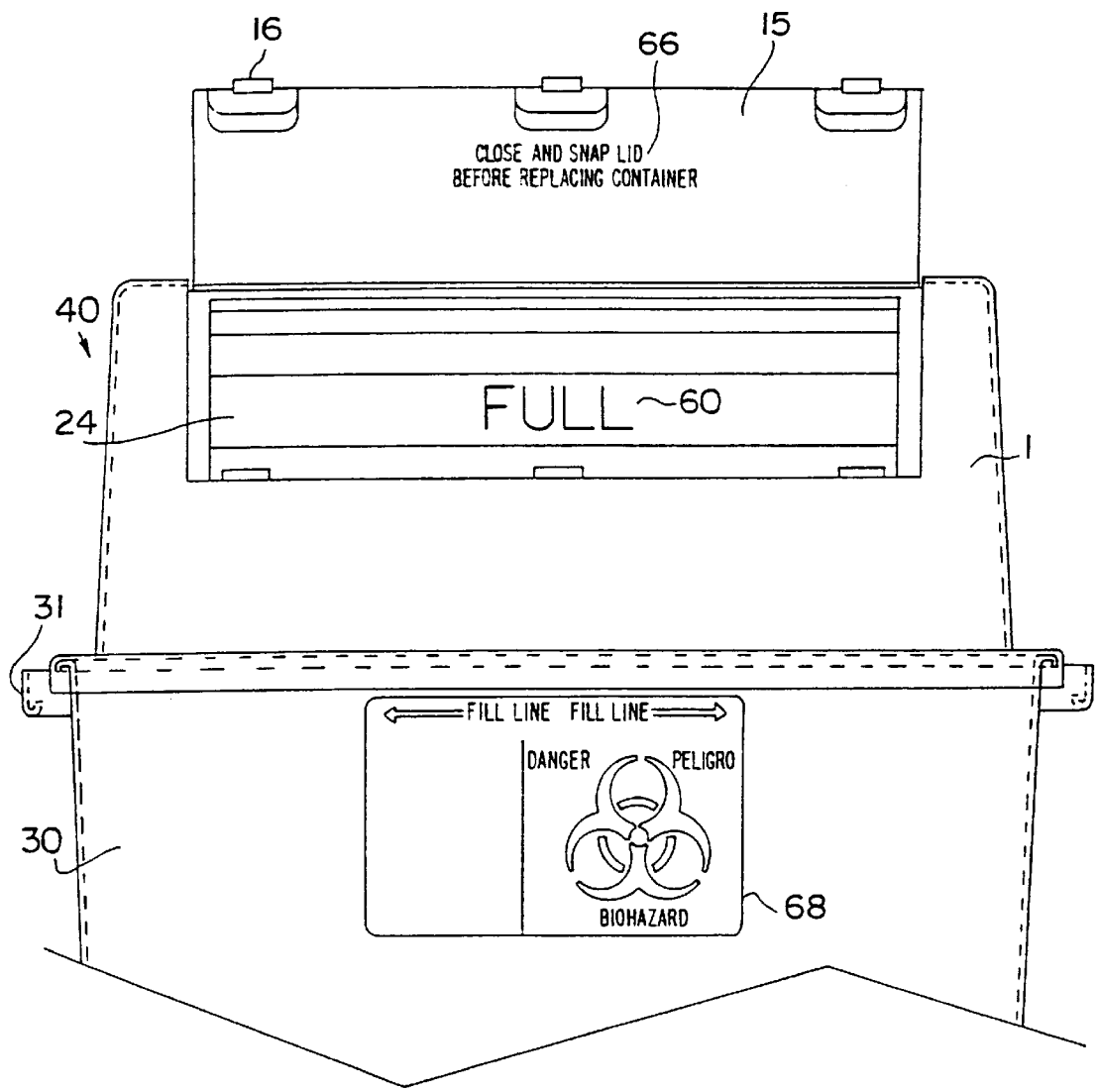
FIG. 8B is a front planar view of the medical waste disposal system shown in FIG. 8A.

When disposal container 30 reaches full capacity, tumbler 20 is configured so that it will not return to the open position but remains rotated in a closed position. As shown in FIG. 8A, when disposal container 30 is filled, tumbler 20, which is rotated to close upper opening 3, is blocked from rotation in the opposite direction by the last sharp deposited. In this blocked orientation in the closed position, tumbler 20 does not permit any more waste to be deposited because upper opening 3 remains closed. An indicator 60 is also provided to easily and quickly inform a user by a cursory inspection of disposal system 40 that disposal container 30 is filled and that the user should not attempt to deposit any more waste. As shown in FIG. 8B, indicator 60 may comprise printing or stamping the word "FULL" into the area of lower portion 24 of tumbler 20 which appears in plain view of a user in upper opening 3 when tumbler 20 is blocked in the closed position.

Figure 8C:
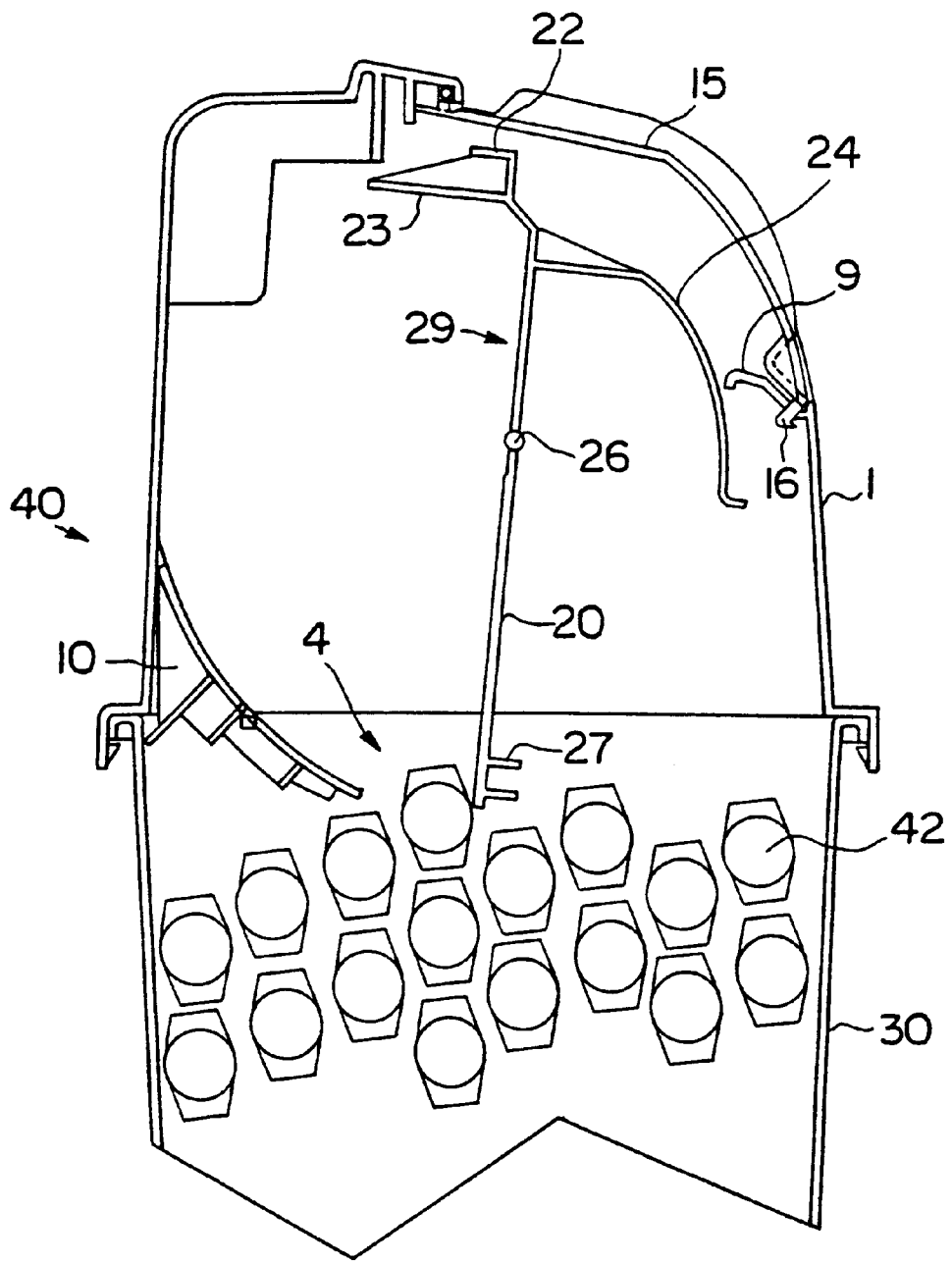
FIG. 8C is a view similar to FIG. 8A showing a filled disposal container with the lid rotated into the closed position.

At this point, in order to further secure the contents within disposal system 40 when disposal container 30 is filled with waste (or when it is otherwise desired to be discarded), a user can further secure disposal system 40 by closing and locking lid 15 to housing enclosure 1. As shown in FIG. 2A, lid 15, which is shown in the open position, is pivotally mounted to housing enclosure 1 by hinge 18 and has locking tabs 16 which are configured to engage locking aperture 17 of housing enclosure 1. As shown in FIG. 8C, upon rotating lid 15 closed and pressing on locking tabs 16 so that they engage locking aperture 17 in housing enclosure 1, a user may securely close disposal container 30 by covering upper opening 3.

Figure 8D:
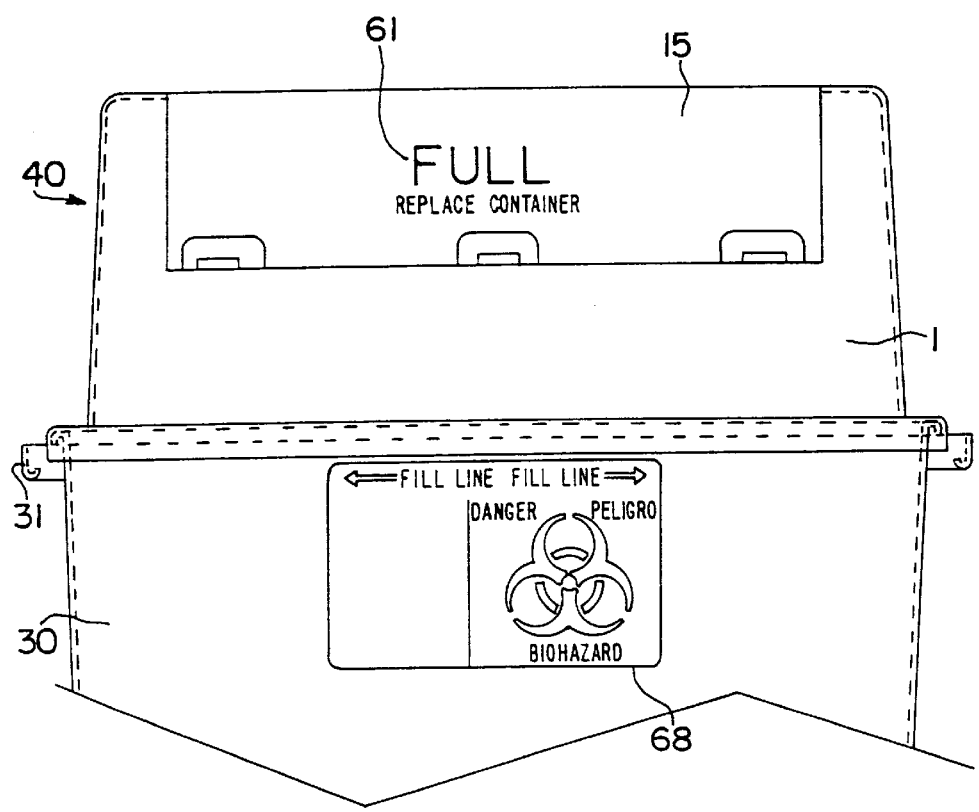
FIG. 8D is a front planar view of the medical waste disposal system shown in FIG. 8C.

Upon closing and locking lid 15 in place, medical waste disposal system 40 is completely secured. This additional security measure further impedes or prevents access to the interior of disposal container 30 after it has been filled and securely closes medical waste disposal system 40 so that it may not be easily reopened. As shown in FIG. 8D, an indicator 61 may be provided on lid 15 which may comprise printing or stamping the word "FULL" into the outer surface of lid 15 to easily and quickly inform a user by a cursory inspection the condition of disposal system 40. As shown in FIGS. 4B, 8B, and 8D, handles 31 may be provided on disposal container 30 to facilitate transporting of disposal system 40.

Figure 10A:
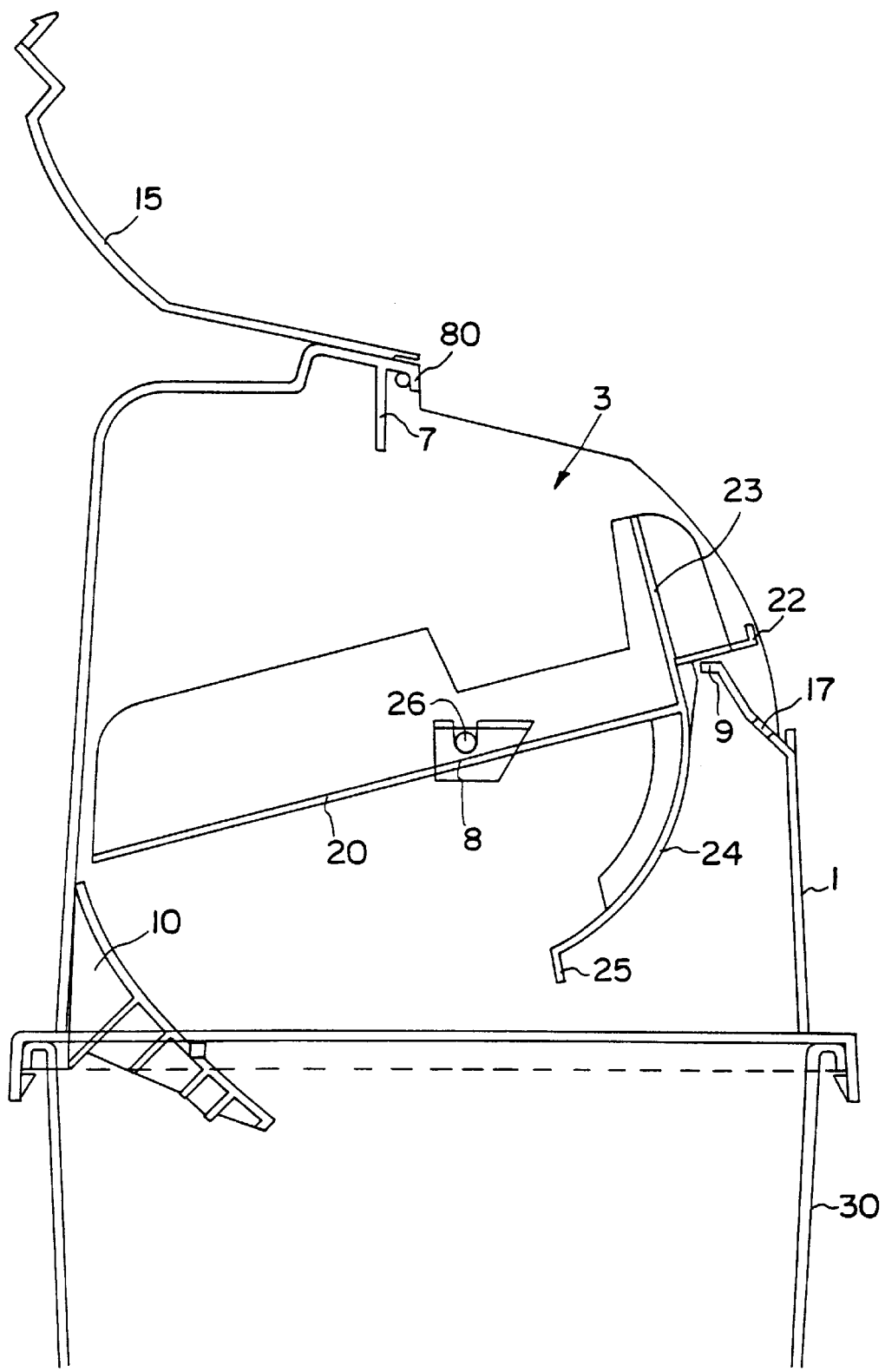
FIG. 10A is a cross-sectional side view of an alternative medical waste disposal system according to the invention, having an additional tumbler configuration, a housing enclosure configuration having an upper stop, and a lid configuration, and with the tumbler in the housing in the fully open position.
Figure 10B:
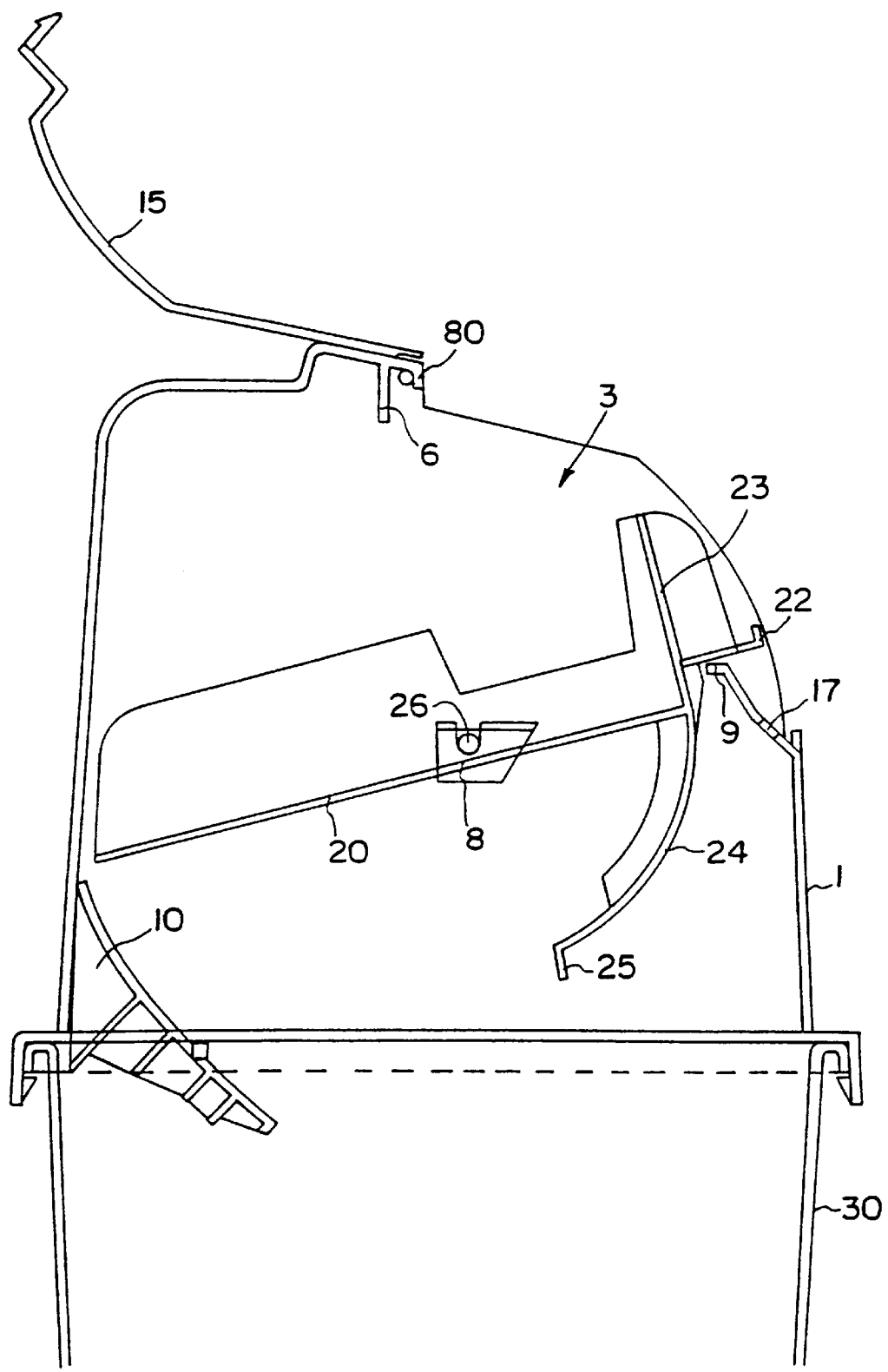
FIG. 10B is a cross-sectional side view of an alternative medical waste disposal system according to the invention similar to that shown in FIG. 10A having an alternative housing enclosure without an upper stop.
Figure 10C:
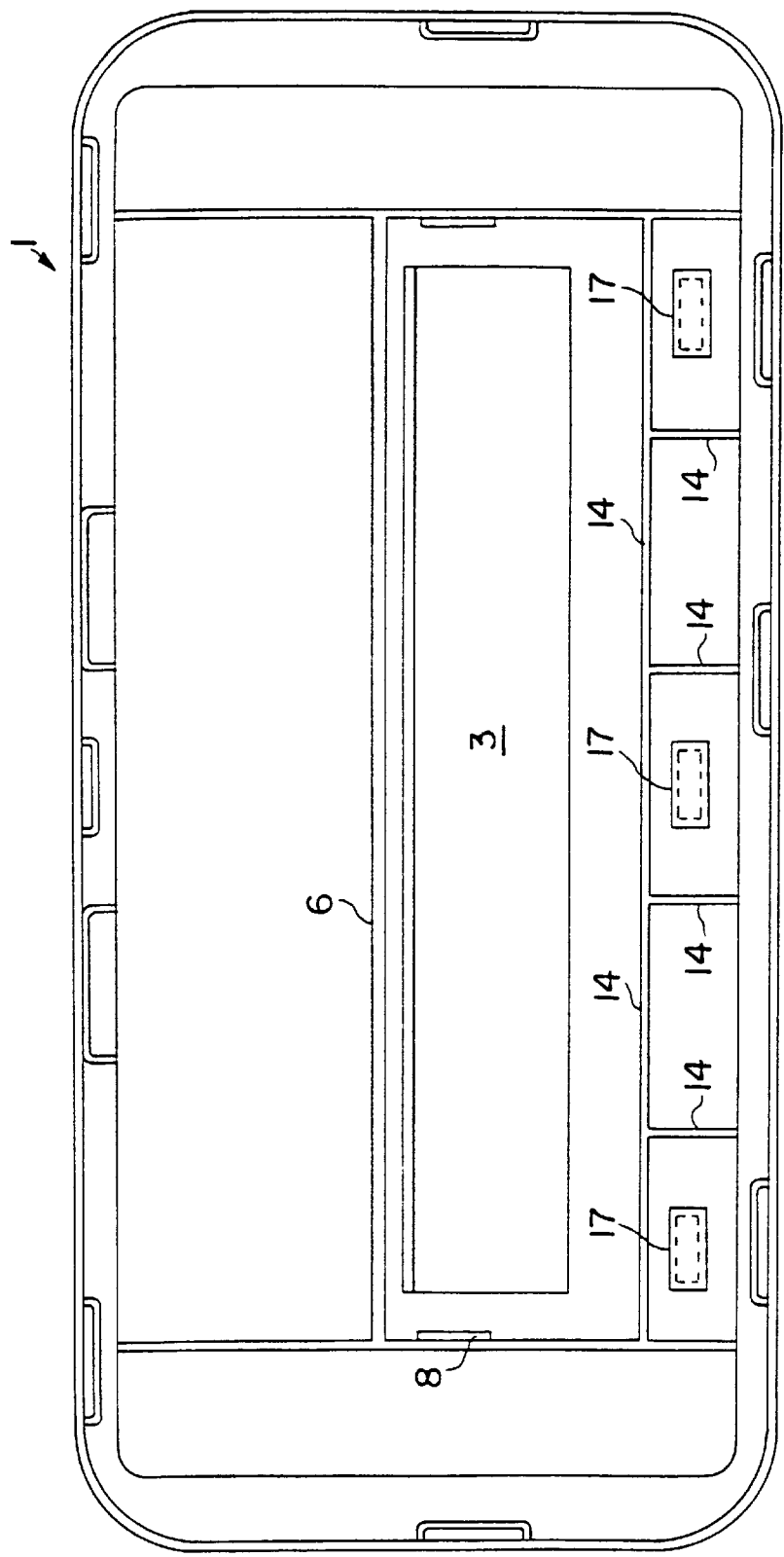
FIG. 10C is a bottom planar view of the housing enclosure shown in FIG. 10B.

As discussed above with respect to FIG. 3, tumbler 20 includes upper portion 23 and curved lower portion 24 which can include a variety of mechanisms to prevent over-rotation of tumbler 20. Shown in FIG. 9A is the use of rib 13 as a stop for upper portion 23 which may be used in conjunction with or as an alternative for a stop provided by flange 25 of curved lower portion 24 which engages lower stop 9 of housing enclosure 1. As shown in FIG. 9B, rib 13 may be configured in a variety of shapes to provide a stop for upper portion 23. Rib 13 may also be extended as shown in FIGS. 12–16. As shown in FIG. 9B, upper portion 23 may be configured to include web 47 which rests upon housing stop 48 provided on housing enclosure 1 when tumbler 20 is in the fully open position shown in FIG. 10D. As shown in FIG. 10A, upper portion 23 may also be configured so that it engages an upper stop 7 in housing enclosure 1 and may be provided as a replacement for or an additional structure to be used with rib 13 for preventing over-rotation of tumbler 20. As shown in FIG. 10A, upper stop 7 is constructed by configuring and positioning reinforcing projections 6 so that they engage upper portion 23 thereby impeding movement of upper portion 23 to prevent over-rotation of tumbler 20.

Alternatives to the stop mechanism provided by flange 25 and lower stop 9 shown in FIGS. 9A and 10A may also be incorporated to prevent over-rotation of tumbler 20. FIGS. 9B and 10D–10K show alternative housing enclosures 1 which incorporate a stop mechanism provided by a scoop 2 which is a curved projection on the inner surface of housing enclosure 1. Scoop 2 has a curved profile which permits lower portion 24 to move freely but prevents over-rotation of lower portion 24 upon rotating tumbler 20. As shown in FIG. 9B, scoop 2 may be added as a back-up stop mechanism to be used in conjunction with an upper stop mechanism such as rib 13 or may be used as the sole stop mechanism for tumbler 20 as shown in FIGS. 10D–10K. The stop mechanism provided by scoop 2 is particularly well-suited for use with tumbler 20 shown in FIG. 9B having an angled tip portion 21 which is discussed in detail below with respect to FIGS. 10D–10K.

Figure 10D:
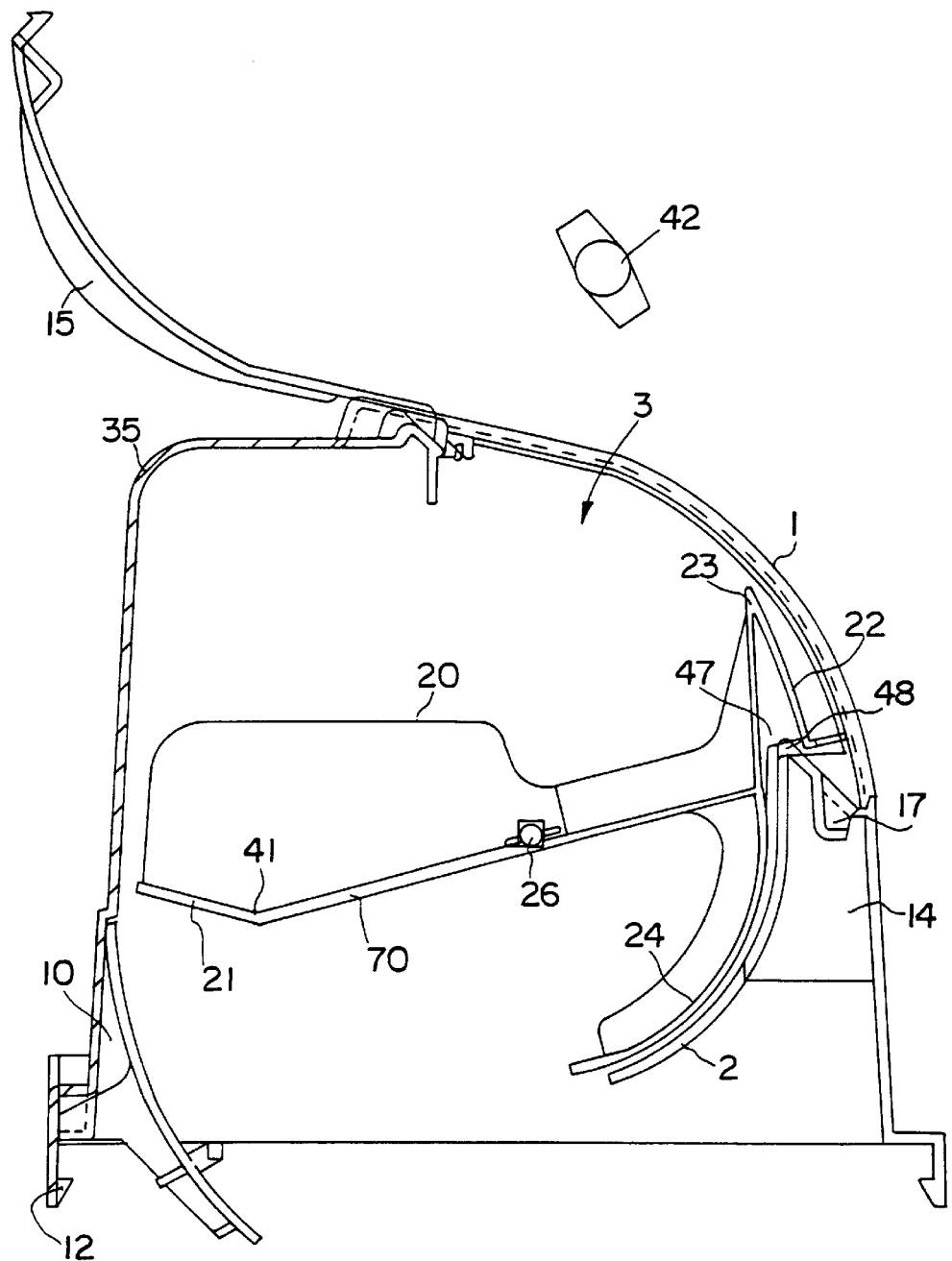
FIG. 10D is an enlarged cross-sectional side view of an alternative embodiment of the medical waste disposal system having a hollow housing enclosure similar to that shown in FIG. 9B, but with the rib reinforcement in the squared contour portion removed and with the tumbler in the housing enclosure in a fully open position and loaded with a sharp to be disposed.

As shown in FIGS. 10A–10K, ribs 13 are not required and may be eliminated from housing enclosure 1 as both a reinforcing structure and a stop mechanism provided that the shape and thickness of housing enclosure 1 are adjusted to accommodate the in-service stresses to which disposal system 40 will be subjected and an alternative stop mechanism is provided for tumbler 20. An exemplary embodiment without ribs 13 is shown in FIG. 10D which has alternative housing enclosure 1 with scoop 2 used in conjunction with tumbler 20 having angled tip portion 21.

Figure 10E:
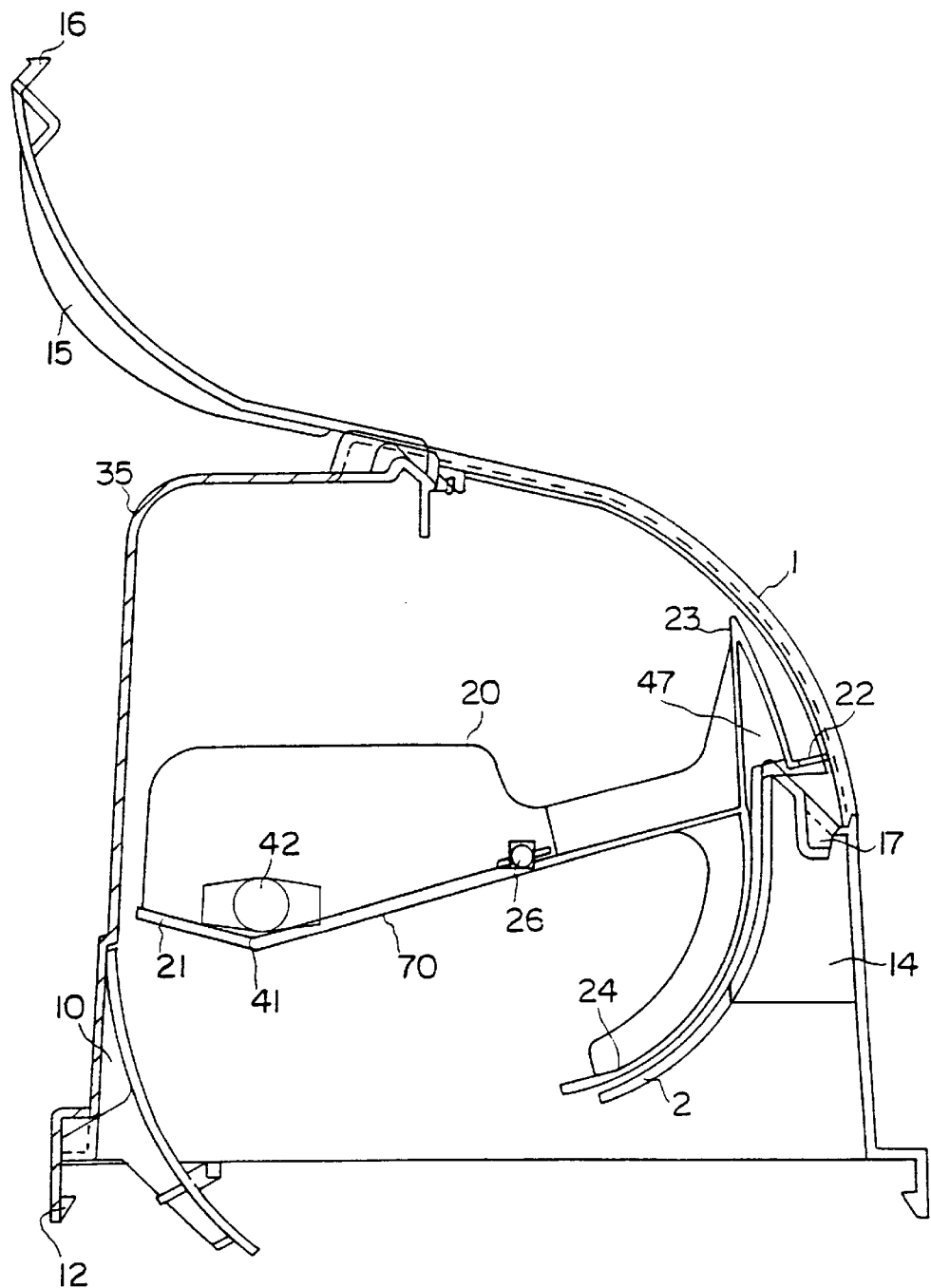
FIG. 10E is a view similar to FIG. 10D, but with the sharp to be disposed shown after sliding to and resting in the crux of the tumbler.

Operation of this embodiment is shown beginning with FIG. 10D in which a used sharp 42 is passed through upper opening 3 of housing enclosure 1 and placed onto tumbler 20 when lid 15 and tumbler 20 are in the open position. The weight of any sharps 42 which are deposited causes tumbler 20 to pivot thereby dropping sharps 42 through lower opening 4 in housing enclosure 1 as shown sequentially in FIGS. 10E–10K. As shown in FIG. 10E, any sharps 42 which are deposited slide along the first straight portion 70 toward angled tip portion 21 of tumbler 20 and rest in crux 41 formed in tumbler 20 between first straight portion 70 and angled tip portion 21.

Figure 10F:
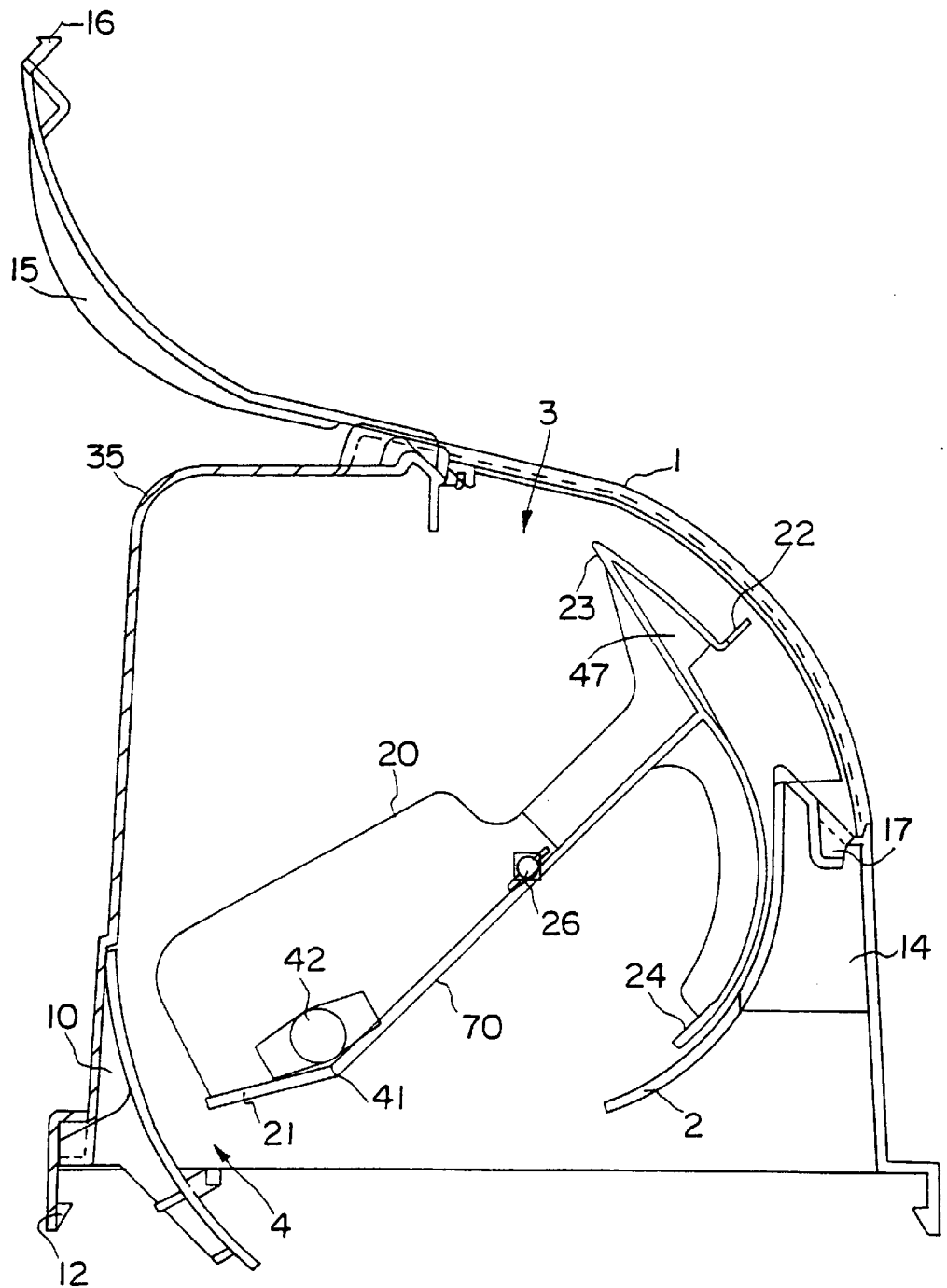
FIG. 10F is a view similar to FIG. 10E, but with the tumbler in the housing enclosure caused to rotate by the weight of the sharp being disposed.
Figure 10G:
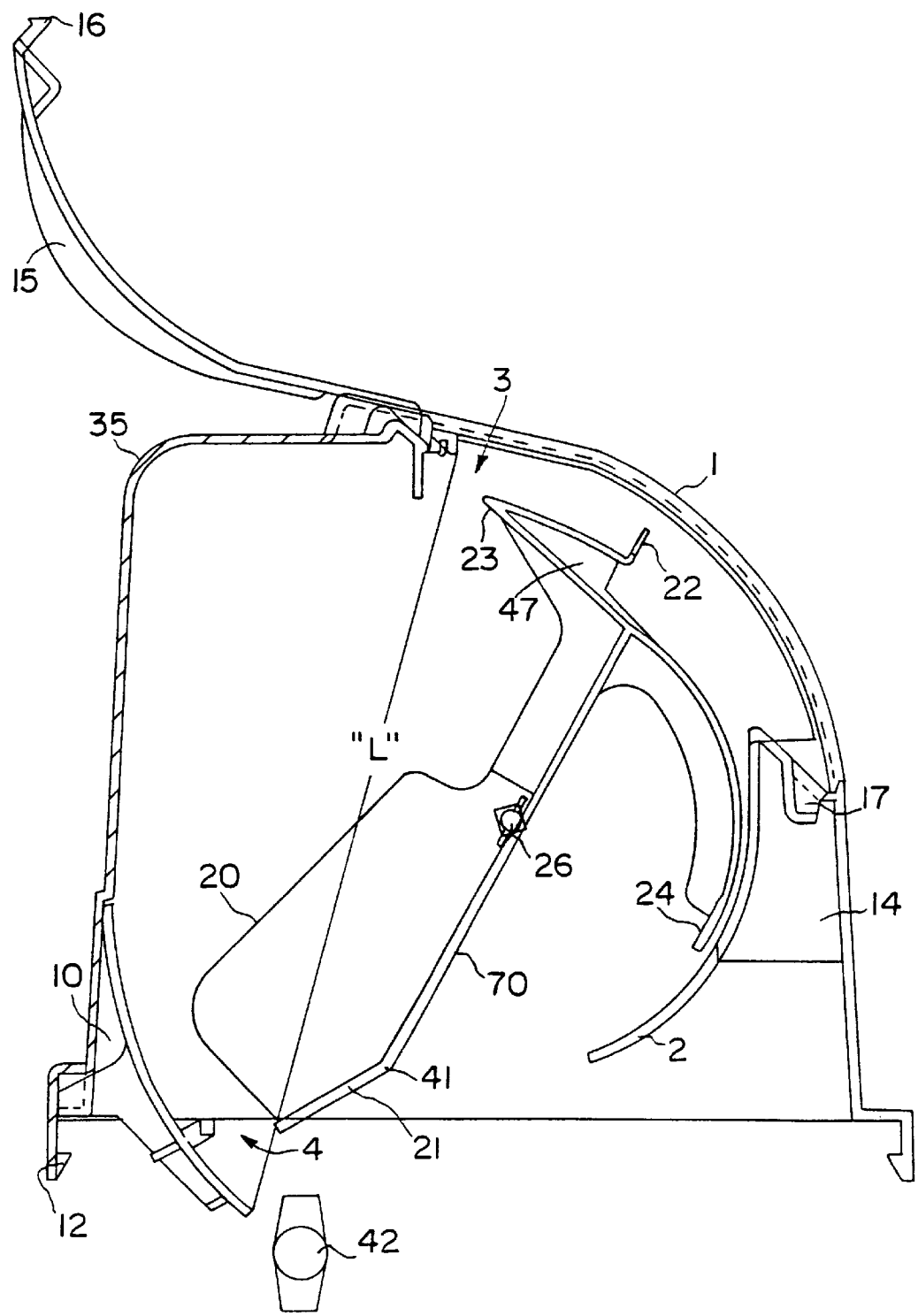
FIG. 10G is a view similar to FIG. 10F, but with the tumbler further rotated to permit the sharp to pass through the lower opening.

The specific angle of angled tip portion 21 is adjusted to maintain sharp 42 on tumbler 20 until angled tip portion 21 is rotated adjacent to flap 10 as shown in FIGS. 10E–10F. Upon further rotation of tumbler 20, as shown in FIG. 10G, sharp 42 slides toward flap 10 and passes between angled tip portion 21 and flap 10 and through lower opening 4. As shown in FIG. 10G, lower opening 4 permits passage of sharp 42 while accessibility beyond the interior of housing enclosure 1 into disposal container 30 is simultaneously blocked as shown by the line of sight designated "L." In this manner, sharp 42 may be safely disposed without the need to fully rotate upper portion 23 to close upper opening 3 which is especially advantageous in the case that tumbler 20 is prevented from rotating to the closed position (e.g., in the case that tumbler 20 becomes jammed).

Figure 10H:
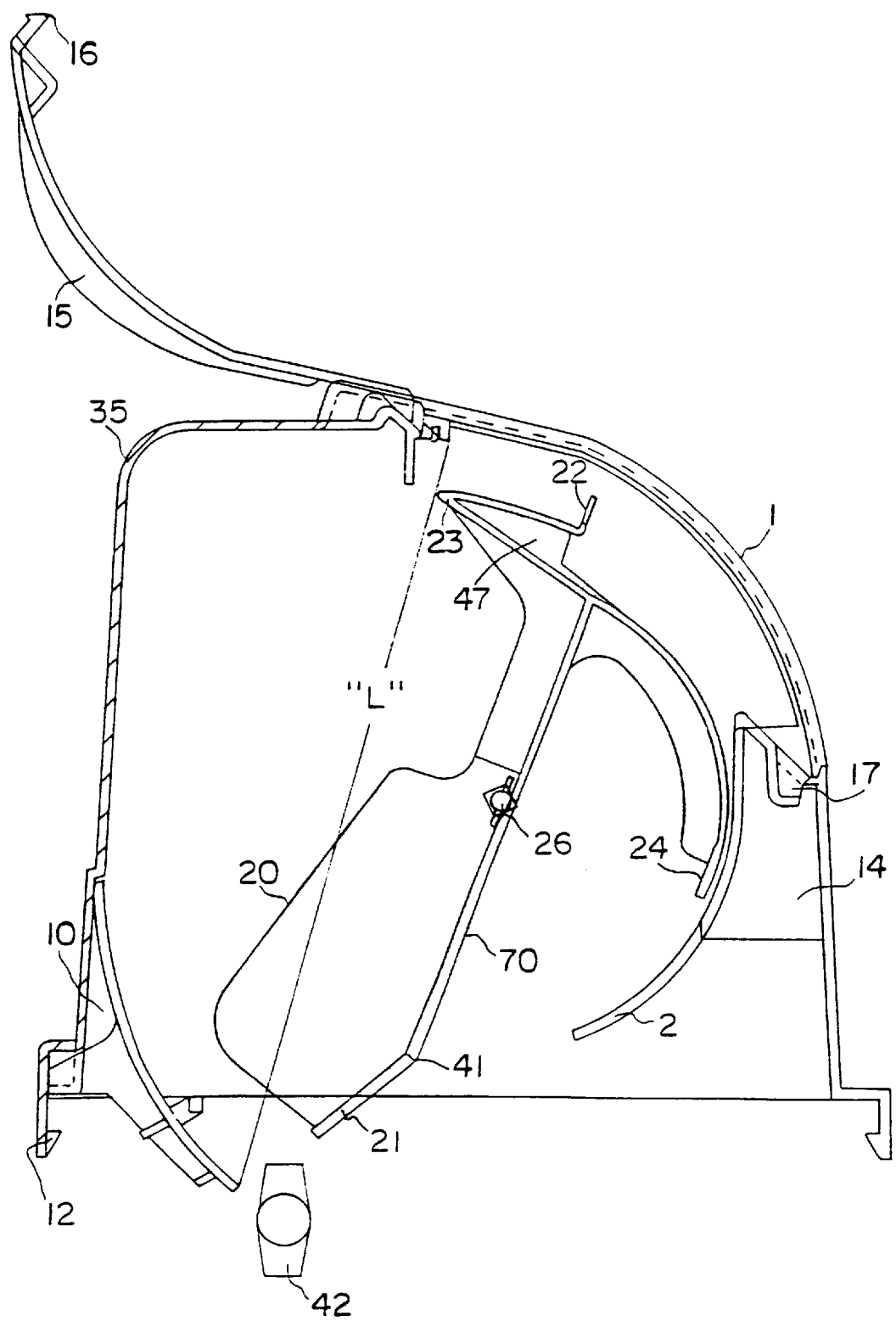
FIG. 10H is a view similar to FIG. 10G, but with the tumbler further rotated to block the upper opening in the housing enclosure from access.
Figure 101:
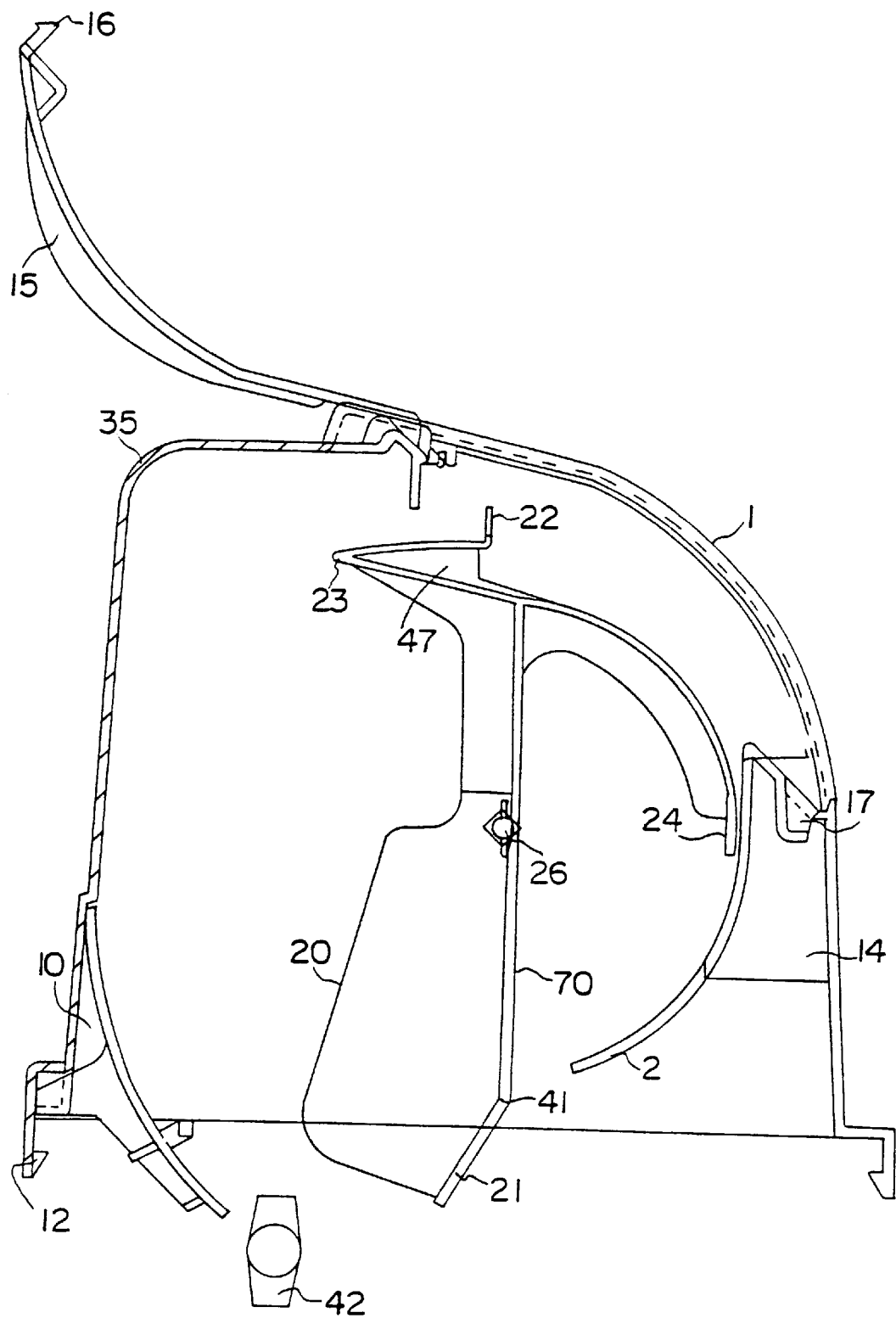
Figure 10J:
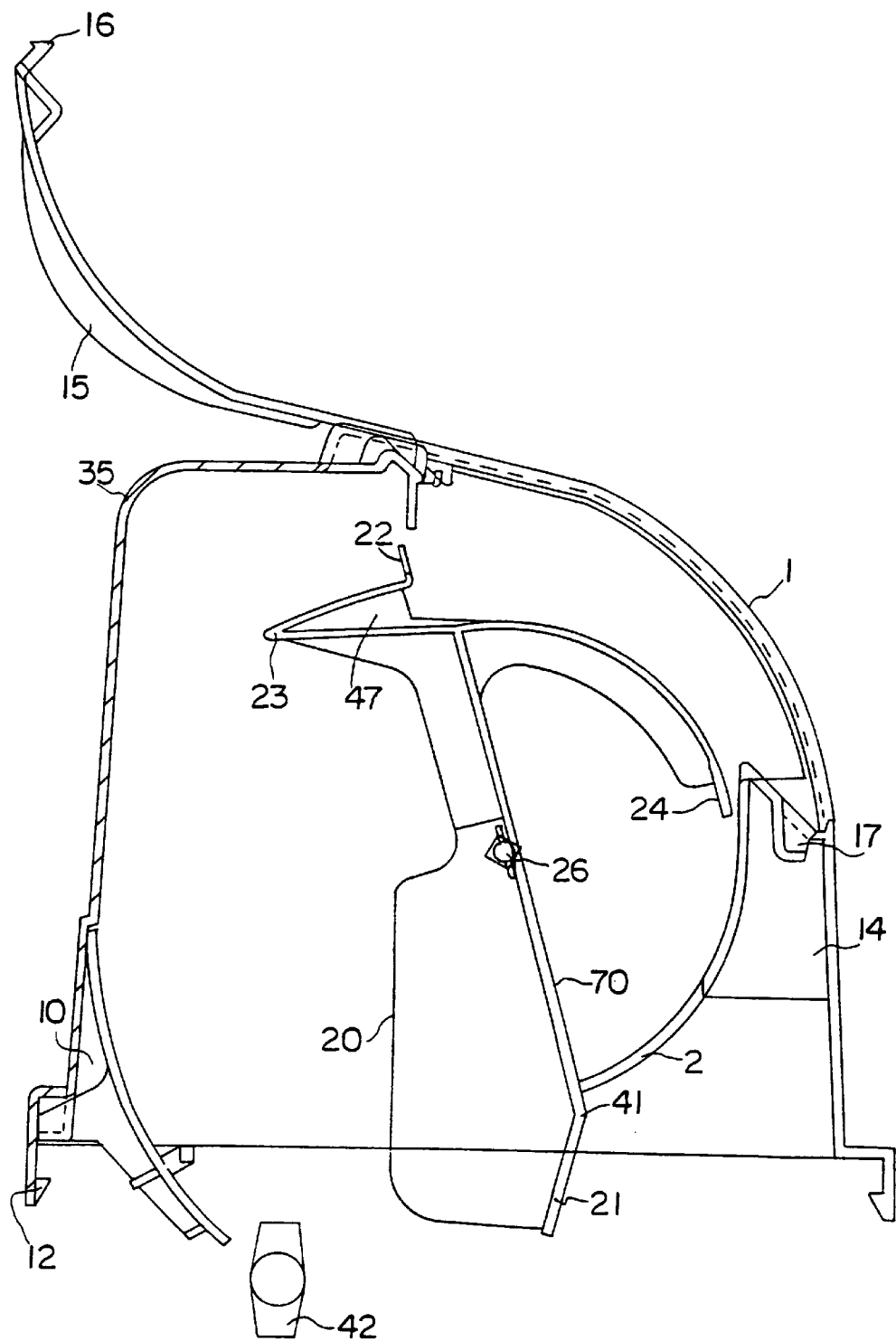
FIG. 10J is a view similar to FIG. 10I, but with the tumbler fully rotated and prevented from further rotation.
Figure 10K:
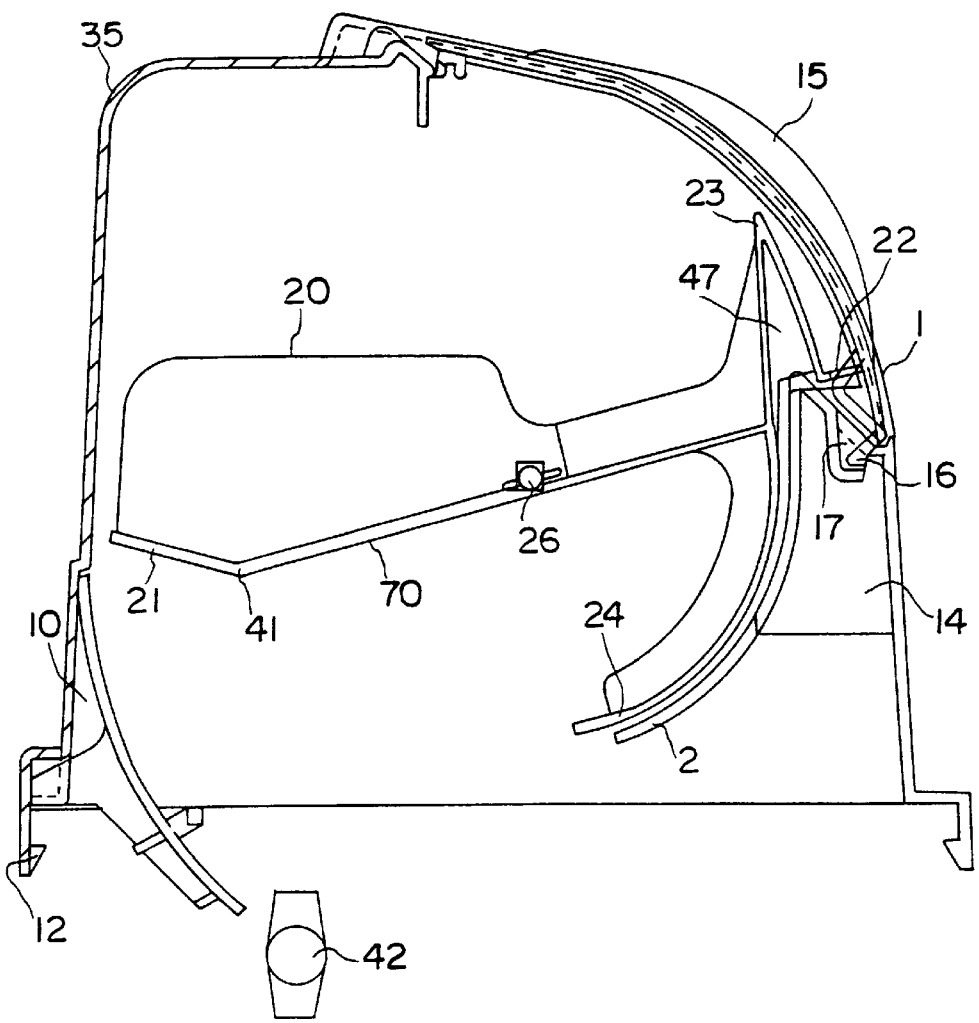
FIG. 10K is a view similar to FIG. 10J after the tumbler returns to the open position and after the lid is rotated into the closed position.
Figure 12:
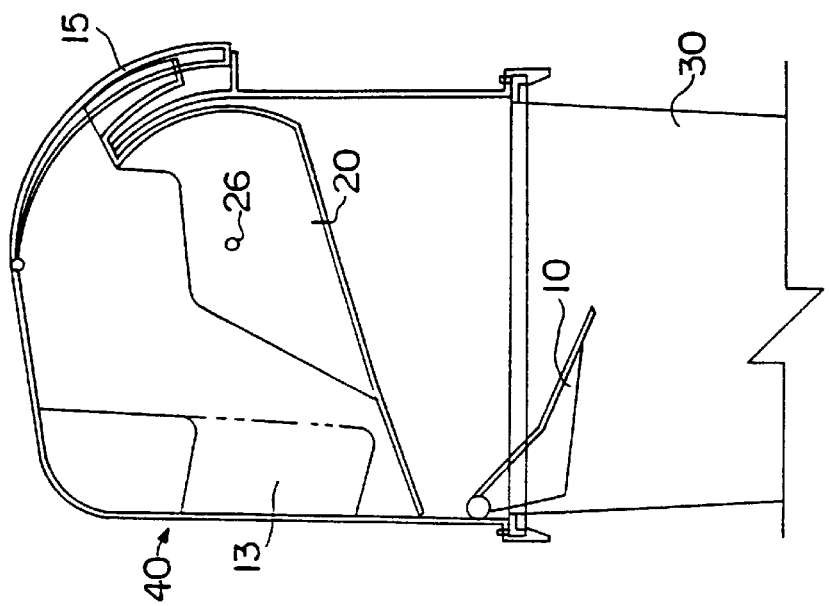
FIGS. 12 and 13 are cross-sectional side views of the medical waste disposal system of the present invention similar to the view of FIG. 1, with the lid in the closed position.

As shown in FIGS. 10H–10J, upon further rotating tumbler 20, upper portion 23 closes upper opening 3 to continuously prevent access to the interior of housing enclosure 1. Over-rotation of tumbler 20 is prevented by scoop 2 which contacts first straight portion 70 of tumbler 20 and prevents further rotation of tumbler 20 as shown in FIG. 10J. As shown in FIG. 10K, upon rotating lid 15 closed and pressing on locking tabs 16 so that they engage locking aperture 17 in housing enclosure 1, a user may securely close and cover upper opening 3 in housing enclosure 1.

As can be seen in FIG. 1, lid or cover 15 according to the present invention is separate from and independent of tumbler 20. This provides the distinct advantage to the user that, in the event of a malfunction of tumbler 20, where tumbler 20 may be jammed in the open or partially open position, the user can simply close lid 15 and lock lid 15 shut, independent of the tumbler position. This differs from other disposal systems which rely on movement of a pivotal closure or tumbler to accomplish both the independent and separate functions of (1) disposing of sharps 42, and (2) locking the housing enclosure and container shut when disposal is complete. Thus, unlike other disposal systems which do not include separate and independent lid 15 and tumbler 20 components, the construction of the present invention allows the user to securely shut and lock waste disposal system 40 at any time, thereby preventing a potentially dangerous situation. Thus, the user is doubly protected from inadvertently extending fingers within disposal container 30.

Disposal system 40 of the present invention also prevents sharps 42 from passing or being ejected back through upper opening 3 of disposal container 30. By shaping the back interior portion of housing enclosure 1 with a squared or sloping contour, sharps 42 which are loaded into housing enclosure 1 are deflected away from upper opening 3. Thus, by shaping housing enclosure 1 in this manner, the present invention eliminates the need for a pivotal closure having a retention pocket to deflect and maintain sharps 42 within disposal container 30.

Figure 11A:
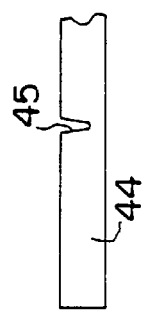
FIG. 11 is a cross-sectional side view of an alternative medical waste disposal system according to the invention, having additional tumbler, housing enclosure, and lid configurations, and with the tumbler in the housing being in the fully open position.
Figure 11:
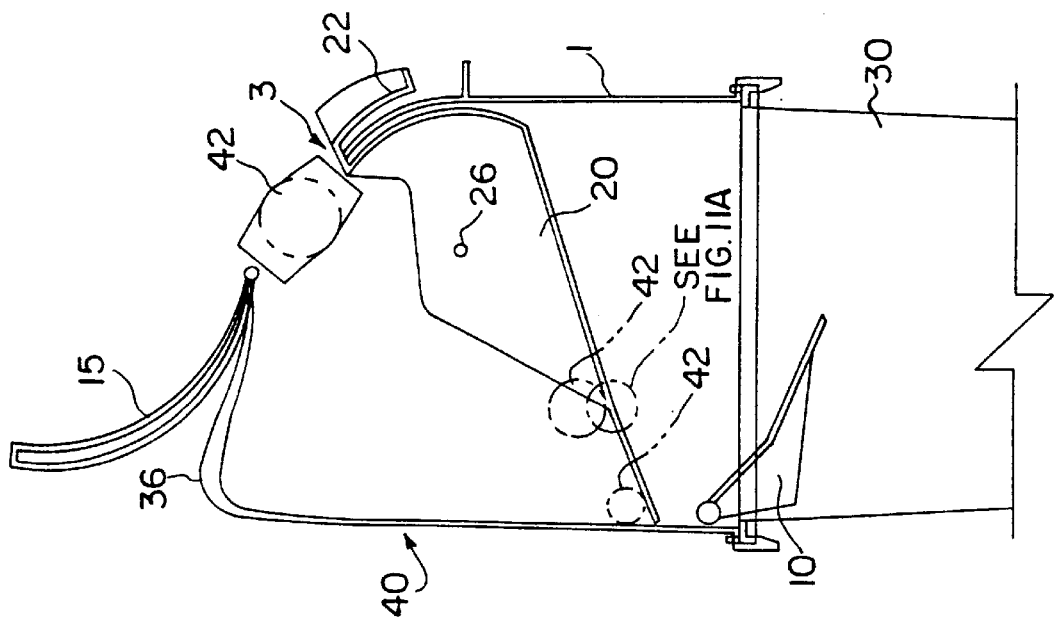
Figure 14:
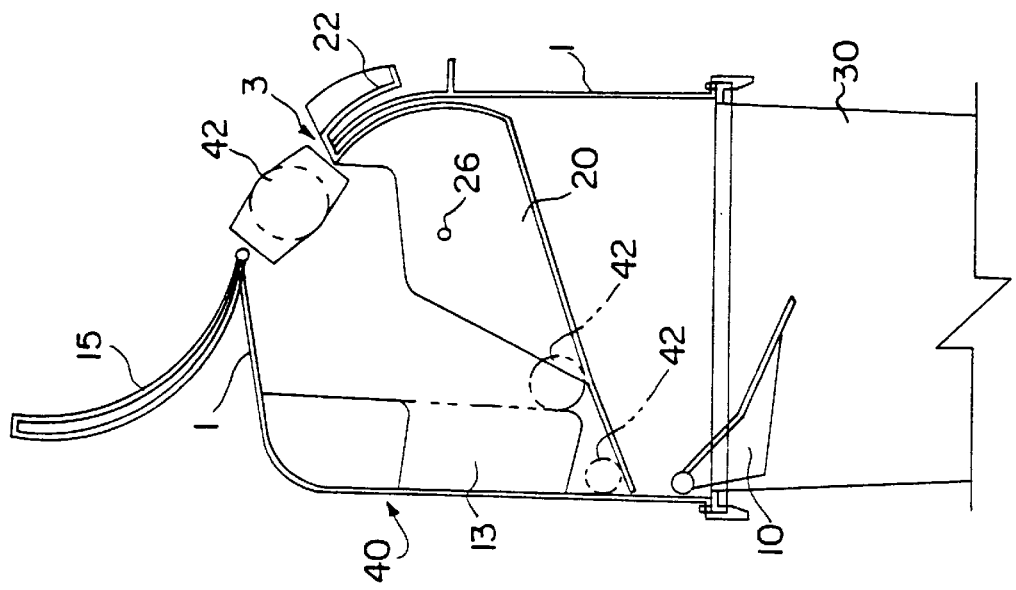
FIG. 14 is a cross-sectional side view of the medical waste disposal system shown in FIG. 13, with the lid in the open position and the tumbler in the housing enclosure in the fully open position and loaded with a large sharp to be disposed.
Figure 13:
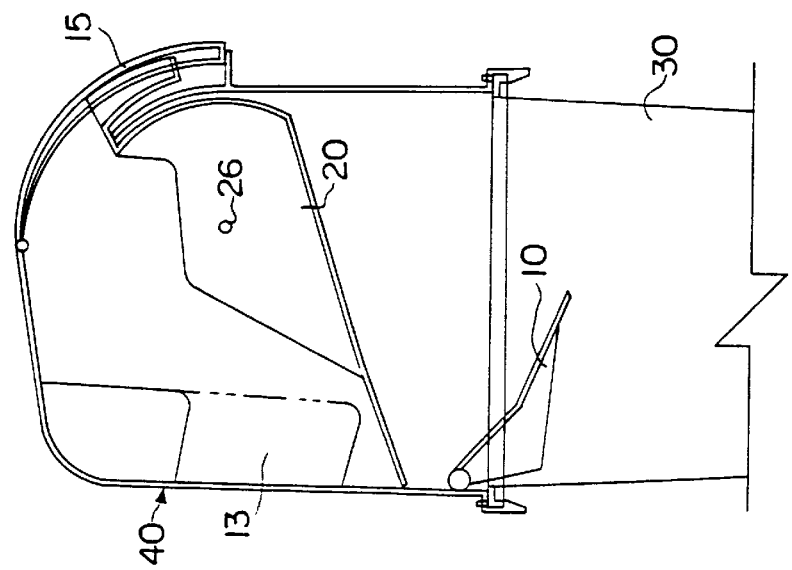
Figure 16:
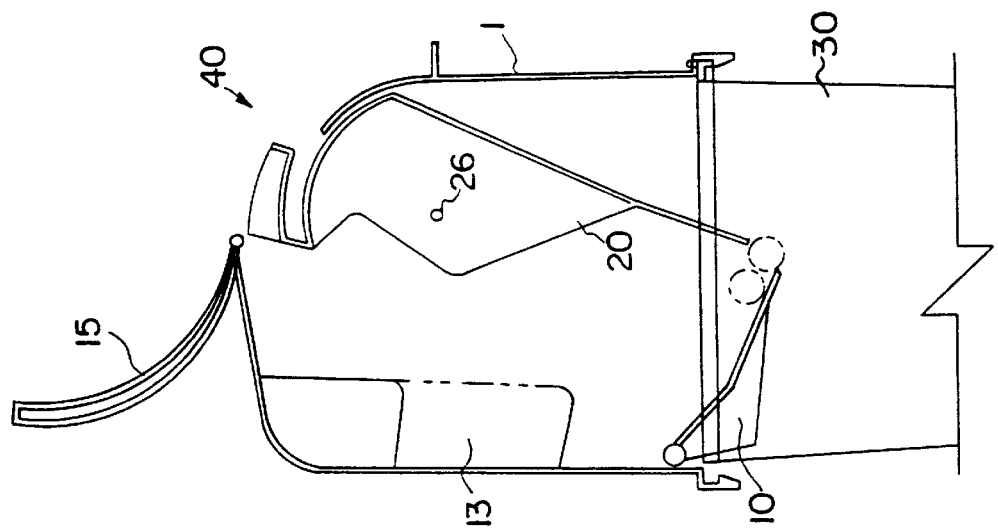
FIG. 16 is a view similar to FIG. 15, but with the tumbler positioned immediately after unloading a small sharp to be disposed.
Figure 15:
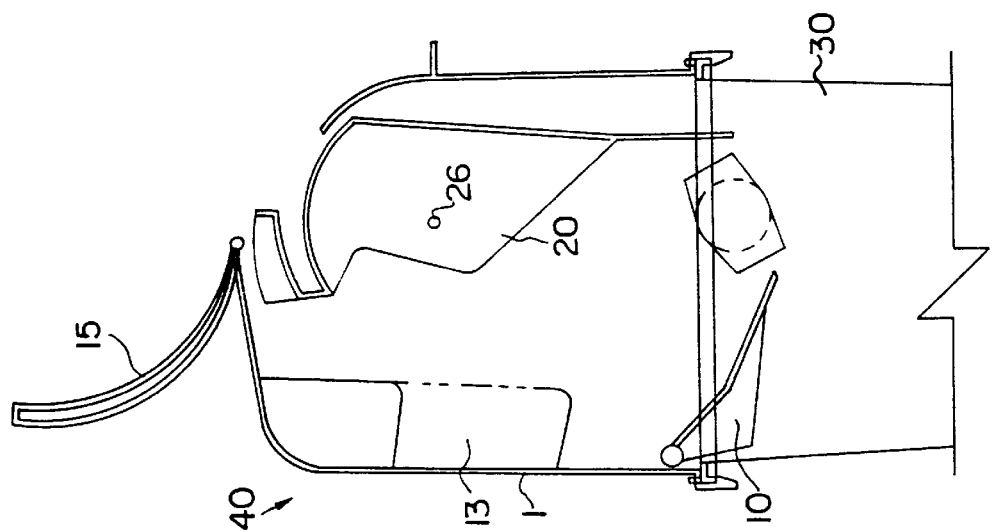
FIG. 15 is a view similar to FIG. 14, but with the tumbler in the housing enclosure approaching the closed position.
Figure 18:
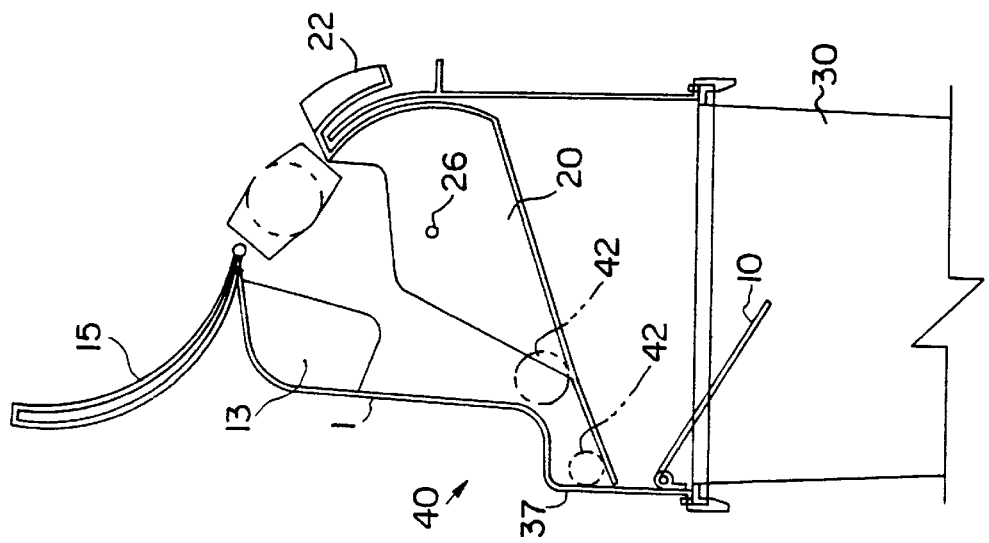
FIG. 18 is a view similar to FIG. 17, with both the lid and the tumbler in the open position and with sharps of various sizes being loaded.
Figure 17:
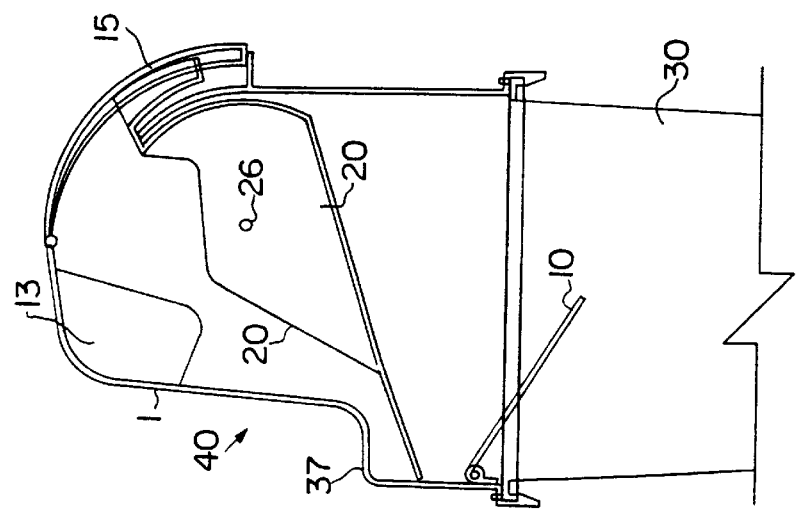
FIG. 17 is a cross-sectional side view of an alternative medical waste disposal system according to the invention, having additional tumbler, housing enclosure, and lid configurations, and with the tumbler in the housing enclosure being in the closed position and the lid closed.
Figure 20:
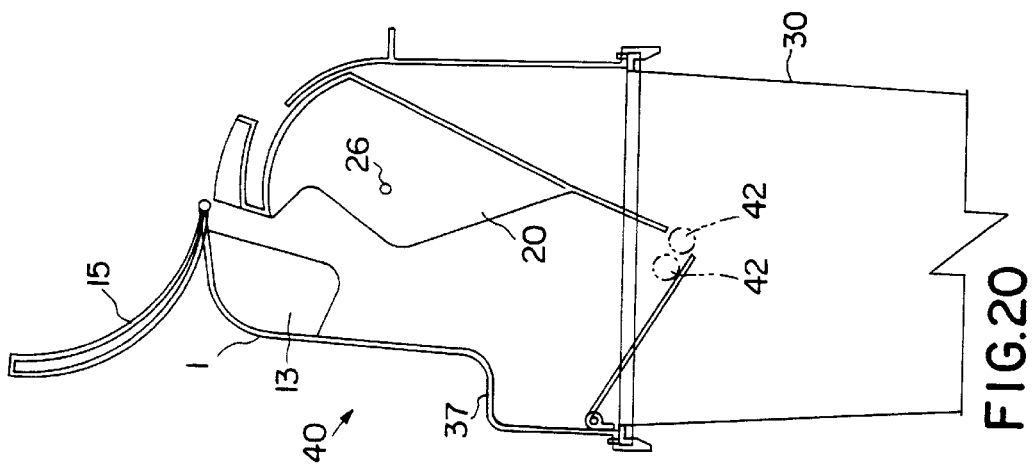
FIG. 20 is a view similar to FIG. 18, but with the tumbler in the closed position and with a small sharp being disposed.
Figure 19:
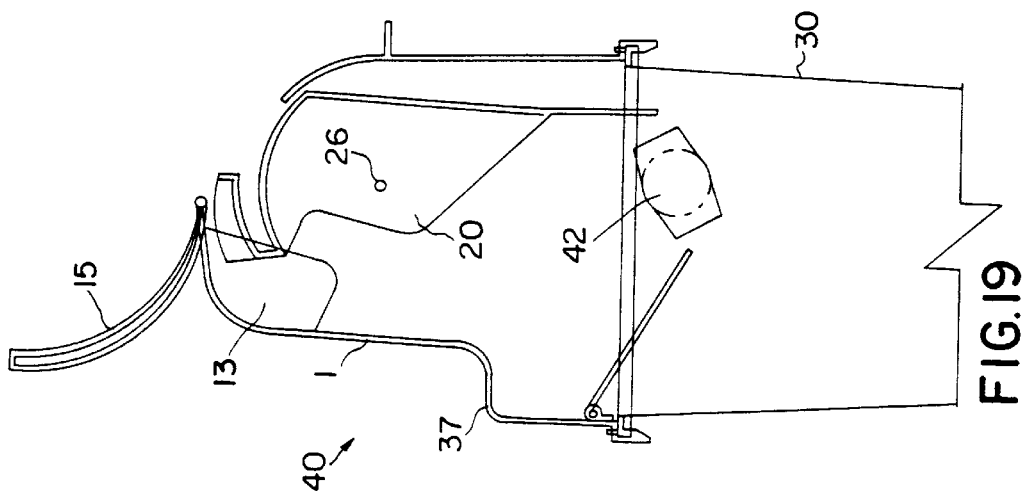
FIG. 19 is a view similar to FIG. 18, but with the tumbler in the closed position and with a large sharp being disposed.

FIG. 1 shows an exemplary housing enclosure 1 having a squared contour portion 35. FIG. 11 shows an exemplary housing enclosure 1 having a sloped contour portion 36 extending downwardly toward upper opening 3. Preferably, sloped contoured portion 36 is formed in a parabolic shape; this shape further enhances the downward deflection of sharps 42. The back portion of housing enclosure 1 may also be configured to have an "S"-shaped portion 37 as shown in FIGS. 17–20.

Also shown in FIG. 11 are two additional features which help to prevent sharps 42 from being ejected from housing enclosure 1, namely, end flap 44 and memory hinge 45 which are incorporated into tumbler 20. By providing tumbler 20 with a memory hinge 45 which is flexible and bendable, end flap 44 is permitted to yield and bend to form an angled tip portion rather than ejecting sharps 42 upon being subjected to any stress created by rotation of tumbler 20. Because it is made of a plastic material having a memory, memory hinge 45 will induce end flap 44 to return to its original, pre-bending position.

As shown by FIGS. 12–20, medical waste disposal system 40 of the present invention may be provided with a variety of housing enclosure 1, tumbler 20, and lid 15 configurations and may be loaded with and used to dispose of medical sharps 42 and other waste in a variety of sizes.

Figure 21A:
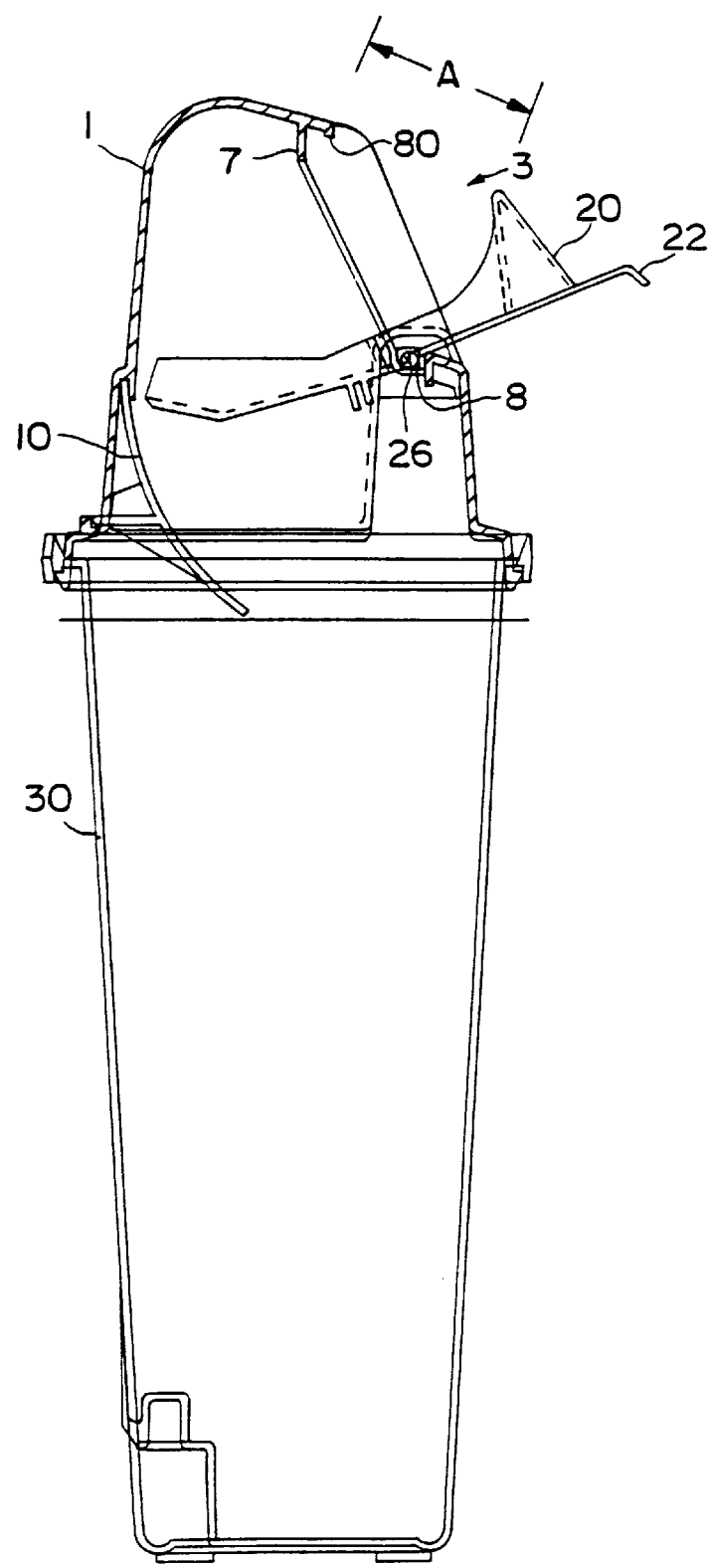
FIG. 21A is a cross-sectional side view of a medical waste disposal system according to another embodiment of the invention, with an alternative form of tumbler located only partially within a hollow housing enclosure and with the tumbler illustrated in the fully open position.
Figure 21B:
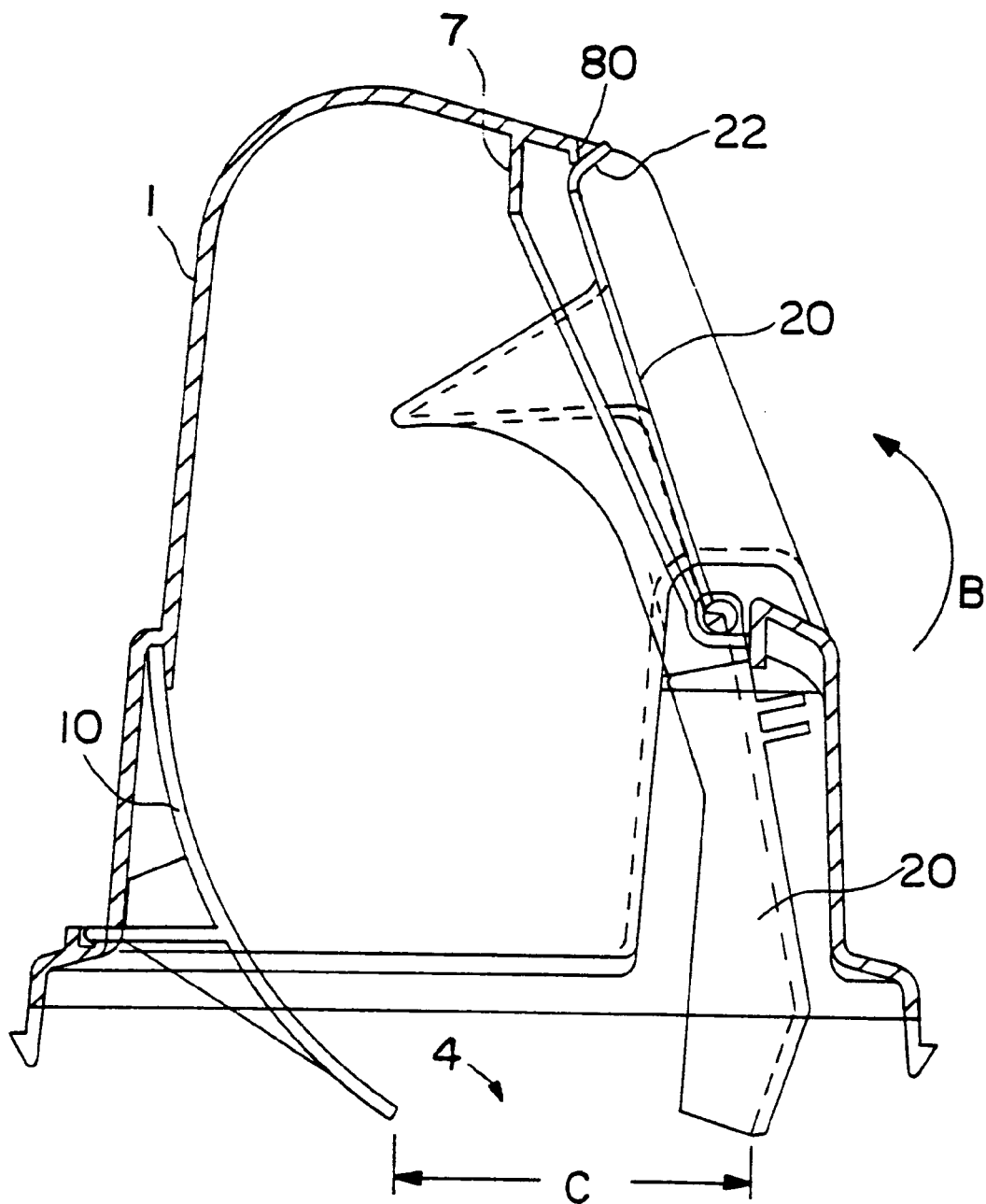
FIG. 21B is an enlarged partial cross-sectional side view of the housing enclosure and tumbler of the medical waste disposal system shown in FIG. 21A with the tumbler fully rotated in its closed position.

FIGS. 21A, 21B, and 21C illustrate yet another embodiment of the waste disposal system 40 of the present invention. In the previous embodiments, tumbler 20 was fully contained within the confines of housing enclosure 1 (although, in some previous embodiments, grip 22 of tumbler 20 extended beyond those confines). As illustrated in FIG. 21A, however, a significant portion of tumbler 20 extends beyond housing enclosure 1, when tumbler 20 is in the fully open position and ready to receive sharp 42 for disposal, in the embodiment shown in FIGS. 21A, 21B, and 21C. The user places sharp 42 on tumbler 20, as for the other embodiments, through upper opening 3. Upper opening 3 may have a dimension "A" of about 41 mm (1⅝ inches). One advantage of this embodiment is that pivot bracket 8 and pivot pins 26 can be formed in the outer wall of housing enclosure 1.

FIG. 21B illustrates tumbler 20 when it has been fully rotated to its closed position in the direction of arrow "B." Grip 22 of tumbler 20 contacts lip 80 on housing enclosure 1 to fully close upper opening 3. At this point, lower opening 4 of housing enclosure 1 is fully open to receive sharp 42 as it passes from housing enclosure 1 into disposal container 30. Like upper opening 3, lower opening 4 may have a dimension "C" of about 41 mm (1⅝ inches).

FIG. 21C shows tumbler 20 in the locked position. Grip 22 performs two functions in the embodiment of waste disposal system 40 shown in FIGS. 21A, 21B, and 21C. First, as in the other embodiments, grip 22 allows the user to manipulate tumbler 20. In this embodiment, however, grip 22 also provides a mechanism to lock tumbler 20 and securely close upper opening 3. Specifically, when disposal container 30 is full, the user can push grip 22 past lip 80 and into engagement with upper stop 7 on housing enclosure 1. This locks grip 22 between lip 80 and upper stop 7 and, therefore, locks tumbler 20 into a closed position over upper opening 3. Thus, it is possible to eliminate lid 15 in this embodiment.

Figure 22:
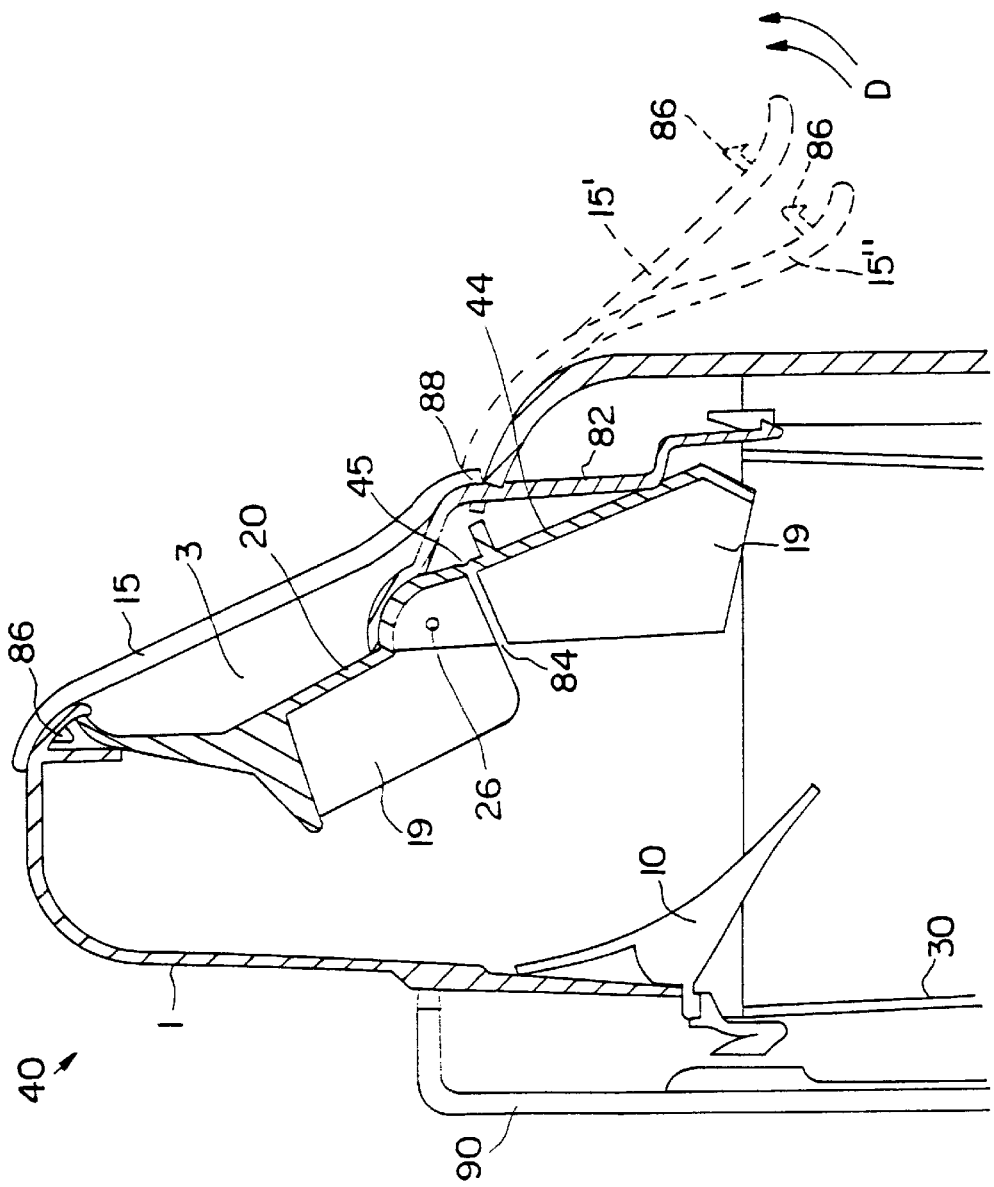
FIG. 22 is a cross-sectional side view of a medical waste disposal system according to still another embodiment of the invention, with an alternative form of tumbler located only partially within a hollow housing enclosure having a lid and with the tumbler illustrated in the fully closed position.

FIG. 22 illustrates a final embodiment of the waste disposal system 40 of the present invention. This embodiment combines several features disclosed above with respect to other embodiments. Specifically, like the embodiment of FIGS. 21A, 21B, and 21C, a significant portion of tumbler 20 extends beyond housing enclosure 1 when tumbler 20 is in the fully open position and ready to receive sharp 42 for disposal. (Tumbler 20 is shown in the fully closed position in FIG. 22.) One potential disadvantage of the embodiment of FIGS. 21A, 21B, and 21C is that sharp 42 may become wedged between tumbler 20 and the front wall 82 of housing enclosure 1. If so, the wedged sharp 42 may prevent tumbler 20 from fully closing. The embodiment of waste disposal system 40 shown in FIG. 22 avoids this problem by incorporating the memory hinge 45 of the embodiment shown in FIG. 11.

As for the embodiment of FIG. 11, memory hinge 45 is flexible and bendable, permitting lower portion 24 of tumbler 20 to yield and bend to form an angled tip portion. A groove 84 is formed in tumbler 20, separating side walls 19 into two segments, adjacent to memory hinge 45. Groove 84 provides clearance as tumbler 20 bends about memory hinge 45. For example, groove 84 may simply permit one segment of side walls 19 to slide or otherwise pass by the other segment of side walls 19 (side walls 19 may have a bevel in the area of groove 84 to facilitate such movement) as tumbler 20 bends about memory hinge 45. Alternatively, groove 84 may be sized so that the two segments of side walls 19 do not meet at all as tumbler 20 bends about memory hinge 45. Should a sharp 42 become wedged between lower portion 24 of tumbler 20 and front wall 82 of housing enclosure 1, tumbler 20 will bend about memory hinge 45 into its fully closed position covering upper opening 3.

Memory hinge 45 will induce tumbler 20 to return to its original, pre-bending position because it is made of a plastic material having a memory. Alternatively, rather than a memory hinge, tumbler 20 may have a hinge which simply yields under the pressure exerted by a wedged sharp 42 against tumbler 20. Such a hinge need not be made of a plastic material having a memory; any yielding material would be suitable. A frangible hinge may also be provided which simply breaks when a sharp 42, wedged between lower portion 24 of tumbler 20 and front wall 82 of housing enclosure 1, exerts pressure against tumbler 20.

The final embodiment of the waste disposal system 40 of the present invention illustrated in FIG. 22 also incorporates the advantages of a lid 15. As for the embodiment of FIGS. 21A, 21B, and 21C, grip 22 provides a mechanism to lock tumbler 20 and securely close upper opening 3. The embodiment of FIG. 22 provides a double-locking closure, however, because that embodiment also incorporates lid 15. Lid 15 is shown in the fully closed position in solid lines in FIG. 22. Catch 86 on the end of lid 15 engages a snap-in-slot near the top of housing enclosure 1 to securely lock lid 15 in a closed position over upper opening 3. Lid 15 pivots about holding lugs 88 provided in front wall 82 of housing enclosure 1.

As shown in dashed lines in FIG. 22, lid 15' allows unrestricted access to upper opening 3 in its fully open position. When disposal container 30 is full of sharps 42, tumbler 20 is locked into its closed position over upper opening 3. Then lid 15' is rotated in the direction of arrows "D" into the closed position shown by the solid lines of lid 15. Lid 15' may require post-bending during the closure process to a position represented by the dashed lines of lid 15" in FIG. 22. Brackets 90 may be used to attach waste disposal system 40 to a wall or other suitable mounting structure.

Preferably, housing enclosure 1, tumbler 20, lid 15 (if provided), and disposal container 30 are made of various plastic materials which may be injection-molded. Disposal container 30 and lid 15 may also be made at least partially of a translucent or transparent material so that the contents of disposal container 30 can be viewed easily to facilitate detection of when disposal container 30 is sufficiently full of sharps 42 such that it should be removed and emptied or replaced. It will be readily recognized that other structures, such as a photoelectric sensor and transmitter mounted in disposal container 30, may also be used to determine the level of contents within disposal container 30.

It is envisioned and to be understood that the various configurations of the various components shown in the drawing and used in medical waste disposal system 40 of the present invention, including but not limited to housing enclosure 1, lid 15, tumbler 20, and disposal container 30, may be incorporated either in place of or in combination with any of the configurations disclosed to the extent that the parts are interchangeable. Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A disposal apparatus receiving medical waste, the disposal apparatus comprising:
    a disposal container having a top opening and an interior surface defining a space adapted to collect medical waste to be disposed;
    a housing enclosure positioned over the top opening of the disposal container, the housing enclosure having an interior surface defining an interior, an upper opening permitting access to the interior of the housing enclosure, and a lower opening adjacent to the space in the disposal container;
    a tumbler mounted at least partially within the housing enclosure with an upper portion positioned adjacent the upper opening of the housing enclosure, the tumbler restricting access to the interior of the housing enclosure and adapted to rotate between:
        (a) an open position in which the upper opening is at least partially free of the tumbler to permit loading of the medical waste into the interior of the housing enclosure and the lower opening is blocked by the tumbler, and
        (b) a closed position in which the upper opening is blocked by the tumbler and the lower opening is at least partially free of the tumbler to permit the medical waste to pass from the housing enclosure into the space of the disposal container;
    wherein the medical waste collected in the space of the disposal container blocks the tumbler and prevents rotation of the tumbler when the disposal container is filled with the medical waste, thereby securing the medical waste within the disposal apparatus.

2. A disposal apparatus receiving medical waste, the disposal apparatus comprising:
    a disposal container having a top opening and an interior surface defining a space adapted to collect medical waste to be disposed;
    a housing enclosure positioned over the top opening of the disposal container, the housing enclosure having an interior surface defining an interior, an upper opening permitting access to the interior of the housing enclosure, and a lower opening adjacent to the space in the disposal container;
    a tumbler mounted at least partially within the housing enclosure with an upper portion positioned adjacent the upper opening of the housing enclosure, the tumbler restricting access to the interior of the housing enclosure and adapted to rotate between:
        (a) an open position in which the upper opening is at least partially free of the tumbler to permit loading of the medical waste into the interior of the housing enclosure and the lower opening is blocked by the tumbler, and
        (b) a closed position in which the upper opening is blocked by the tumbler and the lower opening is at least partially free of the tumbler to permit the medical waste to pass from the housing enclosure into the space of the disposal container;
    a lid adapted to cover the upper opening of the housing enclosure; and
    means for rotatably attaching the lid to the housing enclosure.

3. The disposal apparatus according to claim 1, wherein the housing enclosure has a portion, located above the lower opening of the housing enclosure, which is contoured to deflect medical waste received in the housing enclosure away from the upper opening of the housing enclosure and into the disposal container.

4. The disposal apparatus according to claim 3, wherein the portion has a substantially square contour.

5. The disposal apparatus according to claim 3, wherein the portion has a sloped contour extending downwardly toward the upper opening.

6. The disposal apparatus according to claim 3, wherein the portion has a contour which is substantially parabolic.

7. The disposal apparatus according to claim 3, wherein the portion has a substantially S-shaped contour.

8. The disposal apparatus according to claim 1, wherein the housing enclosure has at least one stop mechanism for preventing rotation of the tumbler beyond a predetermined position to maintain the upper opening blocked by the tumbler, the at least one stop mechanism projecting from the housing enclosure and extending into the interior of the housing enclosure.

9. The disposal apparatus according to claim 8, wherein the at least one stop mechanism is selected from the group consisting of a rib, an upper stop, a scoop, and combinations thereof.

10. The disposal apparatus according to claim 1, wherein the tumbler has a flange and the interior surface of the housing enclosure has a stop extending into the interior of the housing enclosure which engages the flange and prevents rotation of the tumbler beyond a predetermined position to maintain the upper opening blocked by the tumbler.

11. The disposal apparatus according to claim 1, wherein the housing enclosure has a stop and the upper portion of the tumbler has a web contacting the housing stop when the tumbler is in the open position.

12. A disposal apparatus receiving medical waste, the disposal apparatus comprising:
 a disposal container having a top opening and an interior surface defining a space adapted to collect medical waste to be disposed;
 a housing enclosure positioned over the top opening of the disposal container, the housing enclosure having an interior surface defining an interior, an upper opening permitting access to the interior of the housing enclosure, and a lower opening adjacent to the space in the disposal container;
 a tumbler mounted at least partially within the housing enclosure with an upper portion positioned adjacent the upper opening of the housing enclosure, the tumbler restricting access to the interior of the housing enclosure and adapted to rotate between:
  (a) an open position in which the upper opening is at least partially free of the tumbler to permit loading of the medical waste into the interior of the housing enclosure and the lower opening is blocked by the tumbler, and
  (b) a closed position in which the upper opening is blocked by the tumbler and the lower opening is free of the tumbler to permit the medical waste to pass from the housing enclosure into the space of the disposal container;
 wherein the tumbler has an end flap engaging the medical waste and a flexible memory hinge disposed proximate the end flap, the memory hinge yielding to prevent the end flap from ejecting the medical waste from the housing enclosure through the upper opening.

13. The disposal apparatus according to claim 1, wherein the tumbler has a chute defined between a pair of opposed walls, each extending to a lower edge portion of the tumbler, preventing the medical waste from wedging during rotation of the tumbler.

14. The disposal apparatus according to claim 1, wherein the tumbler has a counterweight adjusting the center of gravity of the tumbler to bias the tumbler in the open position.

15. A disposal apparatus receiving medical waste, the disposal apparatus comprising:
 a housing enclosure having an interior surface defining an interior, an upper opening permitting access to the interior of the housing enclosure, and a lower opening; and
 a tumbler mounted at least partially within the housing enclosure and having an angled tip portion positioned adjacent to the interior surface of the housing enclosure and an upper portion positioned adjacent the upper opening of the housing enclosure, the tumbler restricting access to the interior of the housing enclosure and adapted to rotate between:
  (a) an open position in which the lower opening is blocked by the tumbler and the upper opening is at least partially free of the tumbler to permit loading of the medical waste onto the tumbler and into the interior of the housing enclosure, and
  (b) a closed position in which the upper opening is blocked by the tumbler and the lower opening is at least partially free of the tumbler to permit the medical waste to pass from the housing enclosure through the lower opening;
 the angled tip portion maintaining the medical waste on the tumbler until the angled tip portion is rotated adjacent to the lower opening, at which point the medical waste passes through the lower opening;
 wherein the housing enclosure has at least one stop mechanism for preventing rotation of the tumbler beyond a predetermined position to maintain the upper opening blocked by the tumbler, the at least one stop mechanism projecting from the housing enclosure and extending into the interior of the housing enclosure.

16. The disposal apparatus according to claim 15, further comprising:
 a lid adapted to cover the upper opening of the housing enclosure; and
 means for rotatably attaching the lid to the housing enclosure.

17. The disposal apparatus according to claim 15, further comprising a disposal container having a top opening and an interior surface defining a space adapted to collect medical waste to be disposed, the housing enclosure disposed over the top opening of the disposal container with the lower opening of the housing enclosure located adjacent to the space in the disposal container.

18. The disposal apparatus according to claim 17, wherein the housing enclosure has a portion located above the lower opening which is contoured to deflect medical waste received in the housing enclosure into the disposal container.

19. The disposal apparatus according to claim 18, wherein the portion has a substantially square contour.

20. The disposal apparatus according to claim 18, wherein the portion has a sloped contour extending downwardly toward the upper opening.

21. The disposal apparatus according to claim 18, wherein the portion has a contour which is substantially parabolic.

22. The disposal apparatus according to claim 18, wherein the portion has a substantially S-shaped contour.

23. The disposal apparatus according to claim 15, wherein the at least one stop mechanism is selected from the group consisting of a rib, an upper stop, a scoop, and combinations thereof.

24. The disposal apparatus according to claim 15, wherein the tumbler has a flange and the interior surface of the housing enclosure has a stop which engages the flange and prevents rotation of the tumbler beyond a predetermined position to maintain the upper opening blocked by the tumbler.

25. The disposal apparatus according to claim 15, wherein the housing enclosure has a stop and the upper portion of the tumbler has a web contacting the housing stop when the tumbler is in the open position.

26. The disposal apparatus according to claim 15, wherein the tumbler has a flexible memory hinge disposed proximate the angled tip portion, the memory hinge yielding to prevent the angled tip portion from ejecting the medical waste from the housing enclosure through the upper opening.

27. The disposal apparatus according to claim 15, wherein the tumbler has a chute defined between a pair of opposed walls, each extending to a lower edge portion of the tumbler, preventing the medical waste from wedging during rotation of the tumbler.

28. The disposal apparatus according to claim 15, wherein the tumbler has a counterweight adjusting the center of gravity of the tumbler to bias the tumbler in the open position.

29. A disposal apparatus receiving medical waste, the disposal apparatus comprising:
 a disposal container having a top opening and an interior surface defining a space adapted to collect medical waste to be disposed;
 a housing enclosure positioned over the top opening of the disposal container, the housing enclosure having an interior surface defining an interior, an upper opening permitting access to the interior of the housing enclosure, and a lower opening adjacent to the space in the disposal container;
 a tumbler mounted at least partially within the housing enclosure, restricting access to the interior of the housing enclosure, and adapted to rotate between (i) an open position in which the upper opening is at least partially free of the tumbler to permit loading of the medical waste into the interior of the housing enclosure and the lower opening is blocked by the tumbler, and (ii) a closed position in which the upper opening is blocked by the tumbler and the lower opening is at least partially free of the tumbler to permit the medical waste to pass from the housing enclosure into the space of the disposal container, the tumbler having:
  (a) an angled tip portion positioned adjacent to the interior surface of the housing enclosure and maintaining the medical waste on the tumbler until the angled tip portion is rotated adjacent to the lower opening, at which point the medical waste passes through the lower opening,
  (b) an upper portion positioned adjacent the upper opening of the housing enclosure, and
  (c) a counterweight adjusting the center of gravity of the tumbler to bias the tumbler in the open position;
 wherein the medical waste collected in the space of the disposal container blocks a closed tumbler in the closed position and prevents rotation of the closed tumbler to the open position when the disposal container is filled with the medical waste, thereby securing the medical waste within the disposal apparatus.

30. A disposal apparatus receiving medical waste, the disposal apparatus comprising:
 a housing enclosure having an interior surface defining an interior, an upper opening permitting access to the interior of the housing enclosure, and a lower opening;
 a tumbler mounted at least partially within the housing enclosure, restricting access to the interior of the housing enclosure, and adapted to rotate between (i) an open position in which the upper opening is free of the tumbler to permit loading of the medical waste into the interior of the housing enclosure and the lower opening is blocked by the tumbler, and (ii) a closed position in which the upper opening is blocked by the tumbler and the lower opening is free of the tumbler to permit the medical waste to pass from the housing enclosure, the tumbler having:
  (a) an end flap,
  (b) a hinge disposed proximate the end flap, and
  (c) an upper portion positioned adjacent the upper opening of the housing enclosure;
 a lid adapted to cover the upper opening of the housing enclosure; and
 means for rotatably attaching the lid to the housing enclosure.

31. The disposal apparatus according to claim 30, further comprising a disposal container having a top opening and an interior surface defining a space adapted to collect medical waste to be disposed, the housing enclosure disposed over the top opening of the disposal container with the lower opening of the housing enclosure located adjacent to the space in the disposal container.

32. The disposal apparatus according to claim 30, wherein the tumbler has a counterweight adjusting the center of gravity of the tumbler to bias the tumbler in the open position.

33. A housing enclosure positionable over a disposal container defining a top opening and a space adapted to collect medical waste to be disposed, the housing enclosure comprising:
 an interior surface defining a housing enclosure interior, an upper opening permitting access to the housing enclosure interior, and a lower opening adjacent to the space in the disposal container;
 a tumbler mounted at least partially within the housing enclosure interior with a portion positioned adjacent the upper opening, the tumbler being pivotally mounted to rotate between:
  (a) an open position in which the upper opening is substantially free of the tumbler to permit loading of the medical waste into the housing enclosure interior and the lower opening is substantially blocked by the tumbler, and
  (b) a closed position in which the upper opening is substantially blocked by the tumbler and the lower opening is substantially free of the tumbler to permit the medical waste to pass from the housing enclosure interior into the space of the disposal container;
 wherein the medical waste collected in the space of the disposal container blocks a closed tumbler in the closed position and prevents rotation of the closed tumbler to the open position when the disposal container is filled with the medical waste, thereby securing the medical waste within the disposal apparatus, and thereby indicating that the disposal container is filled.

34. The housing enclosure according to claim 33, further comprising a ramp extending inwardly from the interior surface of the housing enclosure and toward the space of the disposal container.

35. The housing enclosure according to claim 33, wherein the tumbler is pivotally mounted to the housing enclosure by pivot pins to permit the tumbler to pivot about a pivot axis extending through the pivot pins.

36. The housing enclosure according to claim 33, wherein the interior surface of the housing enclosure has a curvature and wherein the tumbler includes a curved portion having a curvature sufficient to rotate within the curvature of the interior surface of the housing enclosure.

37. The housing enclosure according to claim 33, wherein the tumbler includes a grip positioned to allow ready manipulation of the tumbler by grasping and moving the grip to pivot the tumbler.

38. The housing enclosure according to claim 37, wherein the grip is configured to engage a portion of the housing enclosure.

39. The housing enclosure according to claim 33, wherein the tumbler includes a chute defined between a pair of opposed side walls.

40. The housing enclosure according to claim 33, wherein rotation of the tumbler occurs upon the placement of a predetermined weight of medical waste on the tumbler.

41. A disposal apparatus receiving medical waste, the disposal apparatus comprising:
   a disposal container having a top opening and an interior surface defining a space adapted to collect medical waste to be disposed;
   a housing enclosure positioned over the top opening of the disposal container, the housing enclosure having an interior surface defining an interior, an upper opening permitting access to the interior of the housing enclosure, and a lower opening adjacent to the space in the disposal container;
   a tumbler mounted at least partially within the housing enclosure with a portion positioned adjacent the upper opening of the housing enclosure, the tumbler having a chute defined between a pair of opposed walls each extending toward a lower edge portion of the tumbler, the tumbler restricting access to the space of the disposal container and being pivotally mounted to rotate between:
      (a) an open position in which the upper opening is substantially free of the tumbler to permit loading of the medical waste into the interior of the housing enclosure and the lower opening is substantially blocked by the tumbler, and
      (b) a closed position in which the upper opening is substantially blocked by the tumbler and the lower opening is substantially free of the tumbler to permit the medical waste to pass from the housing enclosure into the space of the disposal container;
   wherein the chute of the tumbler prevents the medical waste from wedging during rotation of the tumbler; and
   wherein the center of gravity of the tumbler is adjusted to bias the tumbler in the open position prior to loading the medical waste into the tumbler.

42. The disposal apparatus according to claim 41, wherein the disposal container is snap-fitted to the housing enclosure.

43. The disposal apparatus according to claim 41, wherein a rib on the housing enclosure prevents over-rotation of the tumbler.

44. The disposal apparatus according to claim 41, wherein the housing enclosure includes a stop surface and the tumbler includes a flange for engaging the stop to prevent over-rotation of the tumbler.

45. The disposal apparatus according to claim 41, wherein a pivot bracket is formed on an outer wall of the housing enclosure to engage a pivot pin on the tumbler to permit rotation of the tumbler.

46. A disposal apparatus receiving medical waste, the disposal apparatus comprising:
   a disposal container having a top opening and an interior surface defining a space adapted to collect medical waste to be disposed;
   a housing enclosure positioned over the top opening of the disposal container, the housing enclosure having an interior surface defining an interior, an upper opening permitting access to the interior of the housing enclosure, and a lower opening adjacent to the space in the disposal container;
   a tumbler mounted at least partially within the housing enclosure with a portion positioned adjacent the upper opening of the housing enclosure, the tumbler restricting access to the space of the disposal container and being pivotally mounted to rotate between:
      (a) an open position in which the upper opening is substantially free of the tumbler to permit loading of the medical waste into the interior of the housing enclosure and the lower opening is substantially blocked by the tumbler, and
      (b) a closed position in which the upper opening is substantially blocked by the tumbler and the lower opening is substantially free of the tumbler to permit the medical waste to pass from the housing enclosure into the space of the disposal container;
   wherein the center of gravity of the tumbler is adjusted to bias the tumbler in the open position prior to loading the medical waste into the tumbler; and
   wherein the housing enclosure has a portion, located above the lower opening of the housing enclosure, which is contoured to deflect medical waste received in the housing enclosure away from the upper opening of the housing enclosure and into the disposal container.

47. The disposal apparatus according to claim 46, wherein the disposal container includes a handle to facilitate transporting of the disposal apparatus.

48. The disposal apparatus according to claim 46, wherein the disposal container, the housing enclosure, and the tumble are injection-molded.

49. The disposal apparatus according to claim 2, wherein the means for rotatably attaching the lid comprises a tab positioned to engage an aperture.

50. The disposal apparatus according to claim 2, wherein the means for rotatably attaching the lid comprises a hinge.

* * * * *

UNITED STATES PATENT AND TRADEMARK OFFICE
CERTIFICATE OF CORRECTION

PATENT NO.    : 5,947,285
DATED         : September 7, 1999
INVENTOR(S)   : Gaba et al.

It is certified that error appears in the above-identified patent and that said Letters Patent is hereby corrected as shown below:

<u>Title page,</u>
Item [56], References Cited, U.S. PATENT DOCUMENTS, insert:
-- 5,154,345    10/1992    Shillington
   5,222,599    06/1993    Boyce
   5,419,435    05/1995    Perzan et al.
   5,560,512    10/1996    Hahn --

Signed and Sealed this

Second Day of December, 2003

JAMES E. ROGAN
*Director of the United States Patent and Trademark Office*